US012263266B2

(12) United States Patent
Ross et al.

(10) Patent No.: US 12,263,266 B2
(45) Date of Patent: Apr. 1, 2025

(54) SYSTEMS AND METHODS FOR DISINFECTION AND SANITATION OF ENVIRONMENTS BY ROBOTIC DEVICES

(71) Applicant: Brain Corporation, San Diego, CA (US)

(72) Inventors: David Ross, San Diego, CA (US); Botond Szatmary, San Diego, CA (US); Louis Gonzalez, San Diego, CA (US)

(73) Assignee: Brain Corporation, San Diego, CA (US)

( * ) Notice: Subject to any disclaimer, the term of this patent is extended or adjusted under 35 U.S.C. 154(b) by 195 days.

(21) Appl. No.: 17/955,082

(22) Filed: Sep. 28, 2022

(65) Prior Publication Data
US 2023/0042650 A1 Feb. 9, 2023

Related U.S. Application Data

(63) Continuation of application No. PCT/US2021/024863, filed on Mar. 30, 2021.
(Continued)

(51) Int. Cl.
*A61L 2/24* (2006.01)
*A61L 2/10* (2006.01)
(Continued)

(52) U.S. Cl.
CPC .................. *A61L 2/24* (2013.01); *A61L 2/10* (2013.01); *A61L 2/22* (2013.01); *G05D 1/0094* (2013.01); *G05D 1/0221* (2013.01); *A61L 2202/11* (2013.01); *A61L 2202/14* (2013.01); *A61L 2202/15* (2013.01); *A61L 2202/16* (2013.01);
(Continued)

(58) Field of Classification Search
CPC ..... A61L 2/24; A61L 2/10; A61L 2/22; A61L 2202/11; A61L 2202/14; A61L 2202/15; A61L 2202/16; A61L 2202/17; A61L 2202/25; G05D 1/0094; G05D 1/0221
See application file for complete search history.

(56) References Cited

U.S. PATENT DOCUMENTS

2004/0244138 A1* 12/2004 Taylor ............... G05D 1/0219
15/319
2014/0305470 A1* 10/2014 Desu-Kalyanam ....................
A46B 13/023
15/36
(Continued)

FOREIGN PATENT DOCUMENTS

| CN | 108664030 A | 10/2018 |
| WO | 2014039076 A1 | 3/2014 |

OTHER PUBLICATIONS

International Search Report and Written Opinion dated Sep. 27, 2021 for PCT/US21/24863.

*Primary Examiner* — Rodney A Butler
(74) *Attorney, Agent, or Firm* — Pierson Ferdinand LLP; Sidharth Kapoor

(57) ABSTRACT

Systems and methods for robotic disinfection and sanitation of environments are disclosed herein. The robotic devices disclosed herein may detect and map locations of pathogens within environments. The robotic devices disclosed herein may utilize data from sensor units to sanitize objects using desired methods specified by operators. The robotic devices disclosed herein may sanitize environments comprising people.

14 Claims, 18 Drawing Sheets

Related U.S. Application Data

(60) Provisional application No. 63/001,717, filed on Mar. 30, 2020.

(51) Int. Cl.
*A61L 2/22* (2006.01)
*G05D 1/00* (2006.01)

(52) U.S. Cl.
CPC ....... *A61L 2202/17* (2013.01); *A61L 2202/25* (2013.01)

(56) References Cited

U.S. PATENT DOCUMENTS

| | | | |
|---|---|---|---|
| 2015/0352605 A1* | 12/2015 | Tiwari | B08B 3/10 134/105 |
| 2016/0271803 A1 | 9/2016 | Stewart | |
| 2016/0287044 A1* | 10/2016 | Tanaka | A47L 9/2857 |
| 2017/0303825 A1* | 10/2017 | Martinson | A61B 5/112 |
| 2017/0361468 A1* | 12/2017 | Cheuvront | G06F 3/16 |

\* cited by examiner

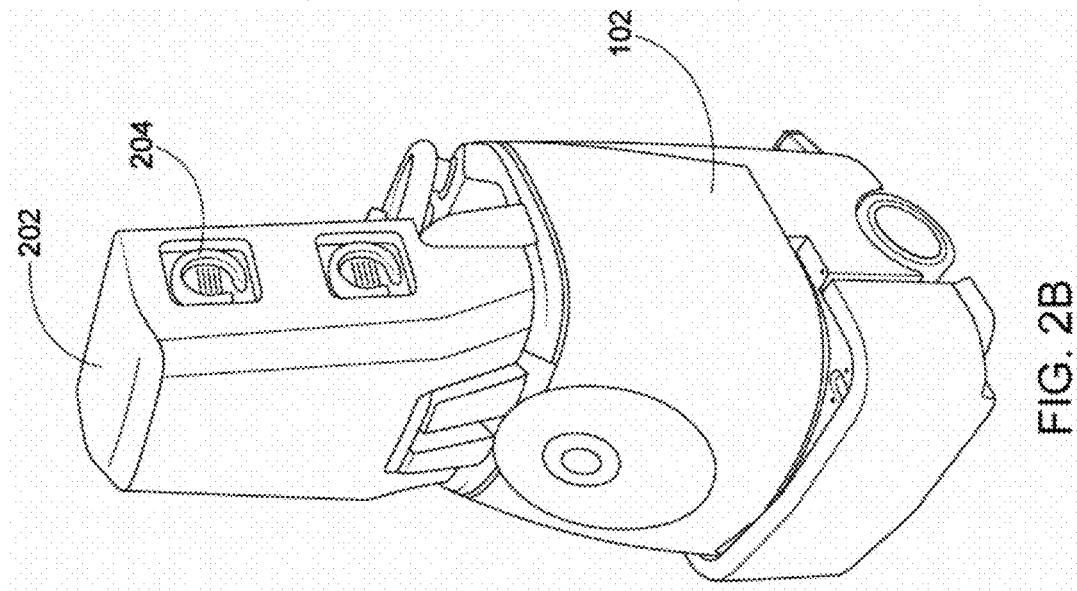

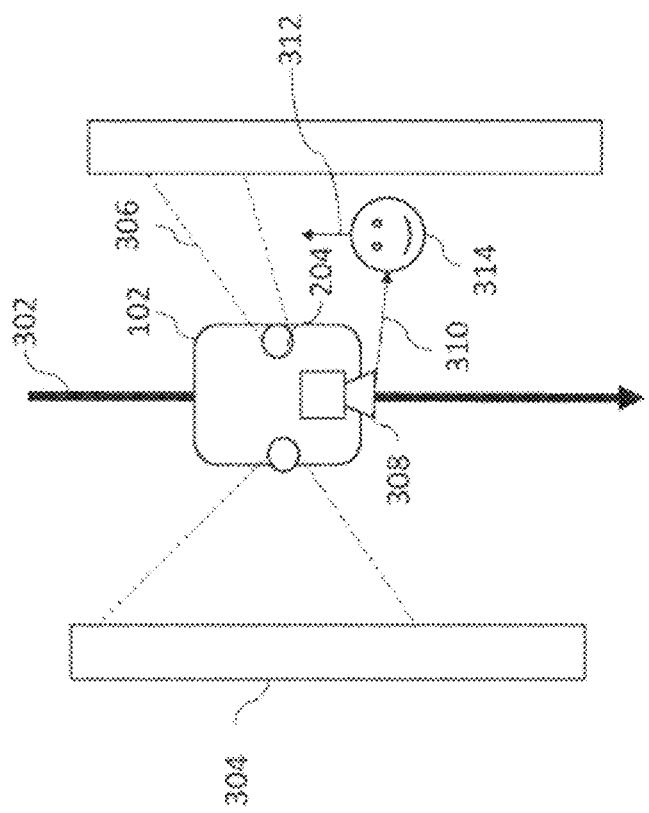

| Object | Action |
|---|---|
| Human | No Action |
| Table | Spray |
| Bed (Unoccupied) | UV |
| Floor | Spray |
| Shelf | UV |
| Wall | UV |
| ... | ... |

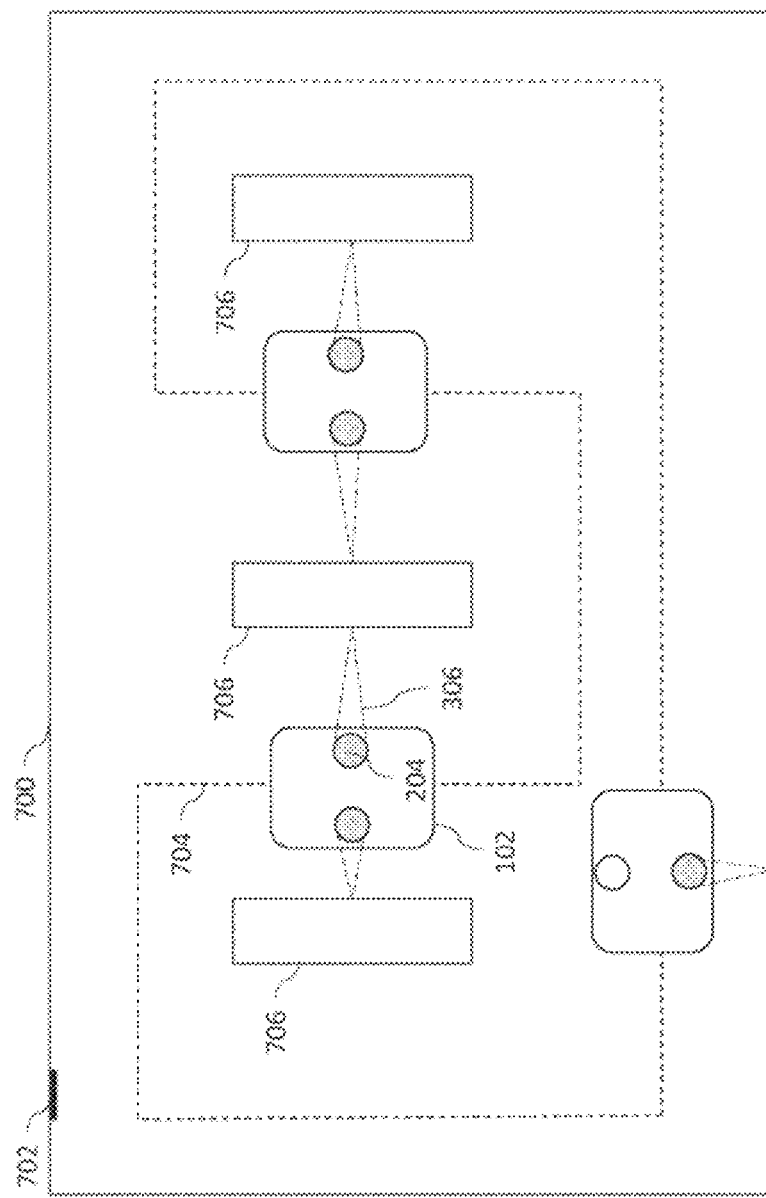

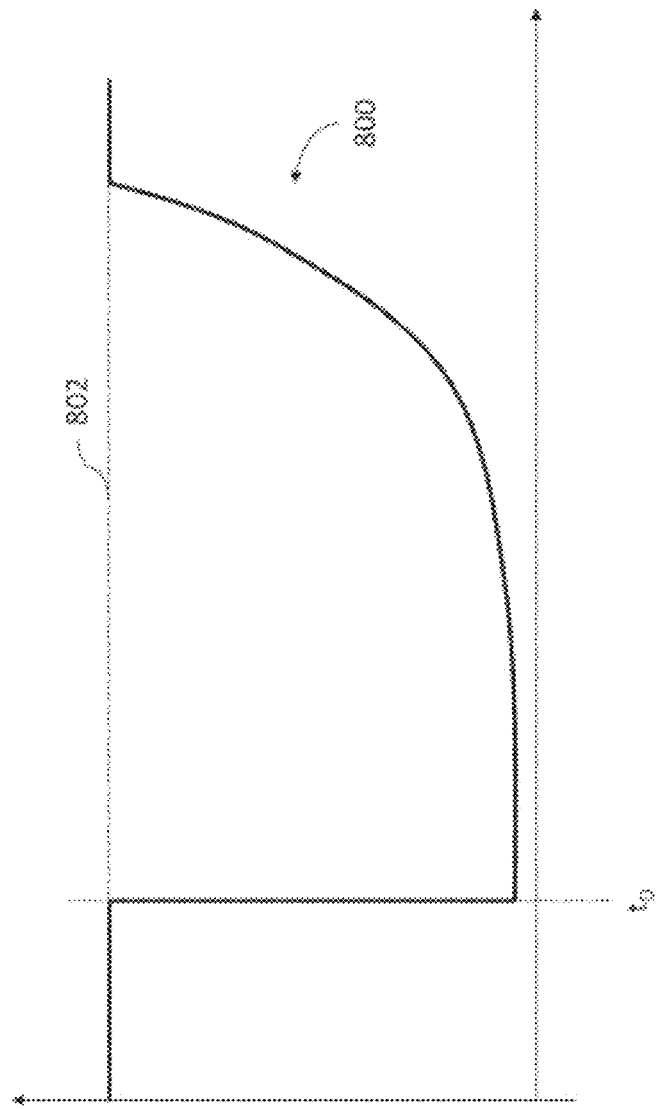

SYSTEMS AND METHODS FOR DISINFECTION AND SANITATION OF ENVIRONMENTS BY ROBOTIC DEVICES

PRIORITY

This application is a continuation of International Patent Application No. PCT/US21/24863, filed Mar. 30, 2021 and claims the benefit of U.S. Provisional Patent Application Ser. No. 63/001,717 filed on Mar. 30, 2020 under 35 U.S.C. § 119, the entire disclosure of each is incorporated herein by reference.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND

Technological Field

The present application relates generally to robotics, and more specifically to systems and methods for robotic disinfection and sanitation of environments.

Background

Currently, the COVID-19 pandemic leaves many medical centers and the general public in need of assistance with sanitation and disinfection of various environments from hospitals to grocery stores. Reducing human exposure to this virus, and other viruses and bacteria, may be critical to reducing growth and spread of the virus. Accordingly, robots are desired to act in lieu of humans in many circumstances to avoid the spread of the virus.

Robots may be equipped with ultra violet ("UV") lights and/or disinfectant sprays, wherein the robots operate with no humans nearby. This enables the robots to disinfect surfaces generally by shining UV light in all directions or spraying any/all surfaces with a disinfectant. However, humans are typically not able to work alongside these robots. This reduces productivity of both the humans and robots. Further, these robots are typically unable to operate in crowded environments, such as grocery stores, where disinfection and sanitization is critical for stemming spread of a pathogen and preserving essential business operations. Social distancing practices may cause many stores, offices, restaurants, etc., to reduce the number of people therein, thereby imposing a larger workload on remaining sanitation workers whose workflow may be effected. Accordingly, there is a need in the art for systems and methods for autonomous robots to disinfect and sanitize environments in which they operate. Further, it is necessary for such autonomous robots to be able to selectively direct UV light or disinfectant sprays to selected surfaces while operating in environments where humans may be present in order to operate in crowded environments.

SUMMARY

The foregoing needs are satisfied by the present disclosure, which provides for, inter alia, systems and methods for robotic disinfection and sanitation of environments.

Exemplary embodiments described herein have innovative features, no single one of which is indispensable or solely responsible for their desirable attributes. Without limiting the scope of the claims, some of the advantageous features will be summarized here. One skilled in the art would appreciate that as used herein, the term robot may generally be referred to autonomous vehicle or object that travels a route, executes a task, or otherwise moves automatically upon executing or processing computer-readable instructions.

This disclosure provides a robotic device, comprising a non-transitory computer-readable storage medium and at least one processor, configured to disinfect an environment using at least one of an ultraviolet light or a disinfectant spray, and avoid directing the ultraviolet light or the disinfectant spray toward a human based on a detection of the human using data from sensor units of the robotic device. One skilled in the art may appreciate that reference to "human" as discussed herein may also consist of pets and other living things that are not inanimate objects.

The robotic device may comprise an ultraviolet emission source configured to emit UV light to kill at least one of germs, viruses, and bacteria, wherein the ultraviolet emission source comprises at least two UV lights, wherein each of the at least two UV lights configured to emit UV light on either side of the robotic device, and at least two UV lights configured to disinfect objects adjacent to the robotic device. Further, wherein at least one controller is configured to execute the computer-readable instruction to orient the robotic device such that field of view of at least two UV lights encompasses objects or surfaces adjacent to the robotic device. Further, wherein at least one controller is configured to execute the computer-readable instruction to change behavior of the robotic device upon detection of the ultraviolet emission source.

According to an example embodiment, wherein the ultraviolet emission source is an attachable module capable of being attached to the robotic device; and wherein the robotic device comprises a plurality of cylindrical UV lights configured to emit UV lights in a plurality of directions. The robotic device comprises an articulated arm configured to adjust position of an ultraviolet emission source. The robotic device comprises a plurality of extendable and retractable features configured to position UV light sources. The plurality of extendable and retractable features comprise actuated portions of the robotic device configured to extend laterally such that the UV light sources are utilized to disinfect a surface including a floor, countertops, tables, and chairs.

According to an example embodiment, the controller is configured to execute the computer-readable instructions to, modulate the UV lights by amplifying or negating the UV lights, enable direction of the UV lights, change intensity of the UV lights, and selectively turn on and turn off the UV lights. Further, wherein the controller is configured to execute the computer-readable instructions to navigate a route along a trajectory, and utilize UV lights to disinfect surfaces of objects positioned along the trajectory.

According to an example embodiment, wherein the controller is configured to execute the computer-readable instructions to, identify a human along a trajectory traveled by the robotic device based on gait pattern of the human, adjust emission of UV lights upon detection of the human such that the UV lights do not interfere with the human along the trajectory, and selectively activate one of at least two UV light sources coupled to the robotic device. The selective activation of a respective of the UV light source is based on location of object with respect to the robotic device, wherein the UV light sources configured to emit light based on shape and size of the object.

According to at least one non-limiting exemplary embodiment, a robot is disclosed. The robot comprises: a non-transitory computer-readable medium having computer-readable instructions stored thereon, and a controller configured to execute the instructions to: update a footprint of robot upon detection of attachment of a sprayer module, the sprayer module being configured to emit a mist of disinfectant solution into an environment; the footprint comprises an area corresponding to a digital representation of the area occupied by the robot, the update of the footprint includes an increase in the area of the footprint, and activates or deactivates the sprayer module in accordance with learned behaviors.

According to at least one non-limiting exemplary embodiment, the computer-readable instructions further configure the controller to: learn a route via user demonstration by recording motions and actions of the robot while the robot operates under manual control, correspond the motions and actions to the learned behaviors, and include at least one activation and deactivation of the sprayer module at one or more locations; and autonomously recreate the route by replicating the motions and activating and deactivating the sprayer module at one or more locations. Stated differently, learned behavior may correspond associating the action undertaken as to the activation or deactivation of the sprayer module and associating the same with a particular location along the route traveled by the robot.

According to at least one non-limiting exemplary embodiment, the robot is configured to perform at least one task such as sweeping floors, vacuuming floors, scrubbing floors, or transporting items from one location to another while the controller is activating or deactivating the sprayer module.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only, and are not intended as a definition of the limits of the disclosure. As used in the specification and in the claims, the singular form of "a", "an", and "the" include plural referents unless the context clearly dictates otherwise.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 2A-E illustrate various exemplary embodiments of a robot configured to disinfect an environment using ultraviolet light.

FIG. 3A-B illustrates a robot utilizing data from sensor units to identify a human and adjust emission of ultraviolet light to avoid illuminating the human, according to an exemplary embodiment.

FIG. 6A illustrates a robot disinfecting items on a shelf using ultraviolet light, according to an exemplary embodiment.

FIG. 7 illustrates a computer-readable map produced as a robot navigates a route to disinfect an environment, according to an exemplary embodiment.

FIG. 8 is a graph which illustrates growth over time of a cleaning parameter used by a robot to determine when the robot should disinfect the environment, according to an exemplary embodiment.

Figure 1A:
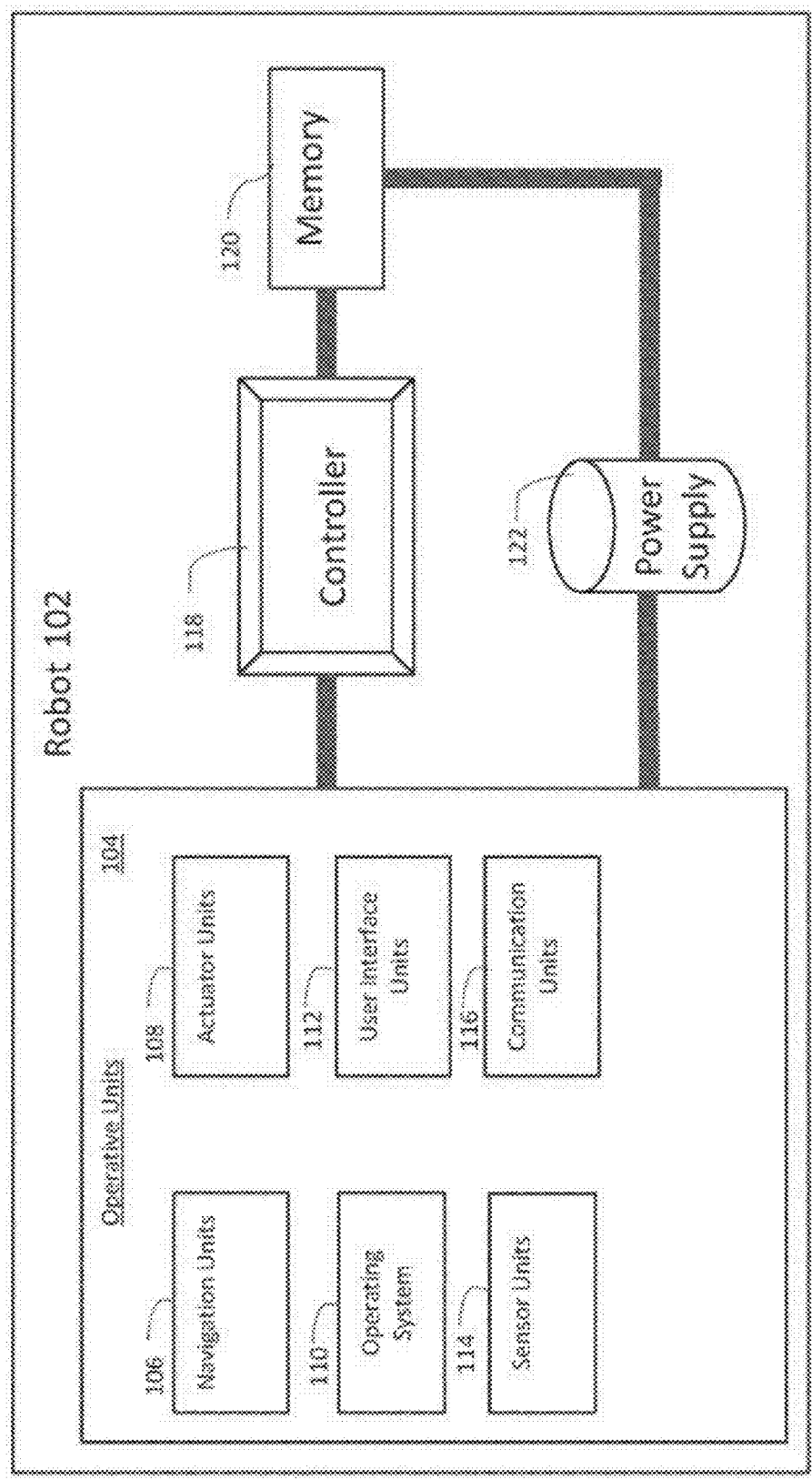
FIG. 1A is a functional block diagram of a robot in accordance with some embodiments of this disclosure.

All Figures disclosed herein are © Copyright 2020 Brain Corporation. All rights reserved.

DETAILED DESCRIPTION

Various aspects of the novel systems, apparatuses, and methods disclosed herein are described more fully hereinafter with reference to the accompanying drawings. This disclosure can, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein, one skilled in the art would appreciate that the scope of the disclosure is intended to cover any aspect of the novel systems, apparatuses, and methods disclosed herein whether implemented independently of, or combined with, any other aspect of the disclosure. For example, an apparatus may be implemented or a method may be practiced using any number of the aspects set forth herein. In addition, the scope of the disclosure is intended to cover such an apparatus or method that is practiced using other structure, functionality, or structure and functionality in addition to or other than the various aspects of the disclosure set forth herein. It should be understood that any aspect disclosed herein may be implemented by one or more elements of a claim.

Although particular aspects are described herein, many variations and permutations of these aspects fall within the scope of the disclosure. Although some benefits and advantages of the preferred aspects are mentioned, the scope of the disclosure is not intended to be limited to particular benefits, uses, and/or objectives. The detailed description and drawings are merely illustrative of the disclosure rather than limiting; the scope of the disclosure being defined by the appended claims and equivalents thereof.

The present disclosure provides for systems and methods for robotic disinfection and sanitation of environments. As used herein, a robot may include mechanical and/or virtual entities configured to carry out a complex series of tasks or actions autonomously. In some exemplary embodiments, robots may be machines that are guided and/or instructed by computer programs and/or electronic circuitry. In some exemplary embodiments, robots may include electro-mechanical components that are configured for navigation, where the robot may move from one location to another. Such robots may include autonomous and/or semi-autonomous cars, floor cleaners, rovers, drones, planes, boats, carts, trams, wheelchairs, industrial equipment, stocking machines, mobile platforms, personal transportation devices (e.g., hover boards, scooters, self-balancing vehicles such as manufactured by Segway, etc.), stocking machines, trailer movers, vehicles, and the like. Robots may also include any autonomous and/or semi-autonomous machine for transporting items, people, animals, cargo, freight, objects, luggage, and/or anything desirable from one location to another.

As used herein, ultraviolet ("UV") light may correspond to light of a wavelength between 200-280 nm, also referred to as UV type C ("UVC") light, used for disinfecting surfaces. Other wavelengths of light may be utilized for eliminating specific pathogens sensitive to other wavelengths using the systems and methods discussed below without detracting from the inventive concepts discussed herein.

As used herein, a pathogen may comprise a virus, bacteria, fungi, protozoa, worm, or microorganism which may cause disease in either humans, animals, or plants. Pathogens may further include any unwanted or undesirable virus, bacteria, or microorganism which may not be harmful to living organisms (e.g., humans and animals) but may be harmful to items within an environment such as, for example, unwanted bacteria in a brewery.

As used herein, a footprint may correspond to a digital representation of area occupied by a robot. Footprints are used by controllers of robots to denote the position, orientation, location, and area occupied by the robot within its environment. Typically, footprints are placed on computer-readable maps of the environment to denote such parameters of the robot. For robots which operate in two dimensions, such as upon flat floors, footprints may comprise of a two-dimensional area occupied by the robot as viewed from the top down on a two-dimensional map. For robots which operate in three dimensions, such as submersibles or drones, the footprint may be a three-dimensional volume in a three-dimensional map. Footprints are often utilized by controllers of robots to check for collisions with nearby objects, wherein overlap of the footprint area and an object on a computer-readable map may indicate a collision between the robot and the object. Footprints of robots are often stored in memory as fixed parameters, shapes, values, structures, etc. if the robot shape does not change. In some instances, however, footprints may be updated to include a different shape or a different area occupied if the robot body shape has changed.

As used herein, network interfaces may include any signal, data, or software interface with a component, network, or process including, without limitation, those of the FireWire (e.g., FW400, FW800, FWS800T, FWS1600, FWS3200, etc.), universal serial bus ("USB") (e.g., USB 1.X, USB 2.0, USB 3.0, USB Type-C, etc.), Ethernet (e.g., 10/100, 10/100/1000 (Gigabit Ethernet), 10-Gig-E, etc.), multimedia over coax alliance technology ("MoCA"), Coaxsys (e.g., TVNET™), radio frequency tuner (e.g., in-band or OOB, cable modem, etc.), Wi-Fi (802.11), WiMAX (e.g., WiMAX (802.16)), PAN (e.g., PAN/802.15), cellular (e.g., 3G, LTE/LTE-A/TD-LTE/TD-LTE, GSM, etc.), IrDA families, etc. As used herein, Wi-Fi may include one or more of IEEE-Std. 802.11, variants of IEEE-Std. 802.11, standards related to IEEE-Std. 802.11 (e.g., 802.11 a/b/g/n/ac/ad/af/ah/ai/aj/aq/ax/ay), and/or other wireless standards.

As used herein, processor, microprocessor, and/or digital processor may include any type of digital processing device such as, without limitation, digital signal processors ("DSPs"), reduced instruction set computers ("RISC"), complex instruction set computers ("CISC") processors, microprocessors, gate arrays (e.g., field programmable gate arrays ("FPGAs")), programmable logic device ("PLDs"), reconfigurable computer fabrics ("RCFs"), array processors, secure microprocessors, and application-specific integrated circuits ("ASICs"). Such digital processors may be contained on a single unitary integrated circuit die or distributed across multiple components.

As used herein, computer program and/or software may include any sequence or human or machine-cognizable steps which perform a function. Such computer program and/or software may be rendered in any programming language or environment including, for example, C/C++, C#, Fortran, COBOL, MATLAB™, PASCAL, GO, RUST, SCALA, Python, assembly language, markup languages (e.g., HTML, SGML, XML, VoXML) and the like, as well as object-oriented environments such as the Common Object Request Broker Architecture ("CORBA"), JAVA™ (including J2ME, Java Beans, etc.), Binary Runtime Environment (e.g., "BREW") and the like.

As used herein, connection, link, and/or wireless link may include a causal link between any two or more entities (whether physical or logical/virtual), which enables information exchange between the entities.

As used herein, computer and/or computing device may include, but are not limited to, personal computers ("PCs") and minicomputers, whether desktop, laptop, or otherwise, mainframe computers, workstations, servers, personal digital assistants ("PDAs"), handheld computers, embedded computers, programmable logic devices, personal communicators, tablet computers, mobile devices, portable navigation aids, J2ME equipped devices, cellular telephones, smart phones, personal integrated communication or entertainment devices, and/or any other device capable of executing a set of instructions and processing an incoming data signal.

Detailed descriptions of the various embodiments of the system and methods of the disclosure are now provided. While many examples discussed herein may refer to specific exemplary embodiments, it will be appreciated that the described systems and methods contained herein are applicable to any kind of robot. Myriad other embodiments or uses for the technology described herein would be readily envisaged by those having ordinary skill in the art, given the contents of the present disclosure.

Advantageously, the systems and methods of this disclosure at least: (i) improve autonomous disinfection of environments; (ii) enable sanitation workers to disinfect larger environments by working alongside robots; (iii) allows for disinfection of populated environments, such as grocery stores or hospitals; (iv) enables robots to determine routes to be executed based on pathogen growth and disinfection of their environments; (v) provide insightful data to workers as to locations of detected pathogens; (vi) improve battery efficiency for robots utilizing ultraviolet light to disinfect surfaces; and (vii) enable robots to disinfect environments using desired methods determined by operators of the robots. Other advantages are readily discernable by one having ordinary skill in the art, given the contents of the present disclosure.

FIG. 1A is a functional block diagram of a robot 102 in accordance with some principles of this disclosure. As illustrated in FIG. 1A, robot 102 may include controller 118, memory 120, user interface unit 112, sensor units 114, navigation units 106, actuator unit 108, and communications unit 116, as well as other components and subcomponents (e.g., some of which may not be illustrated). Although a specific embodiment is illustrated in FIG. 1A, it is appreciated that the architecture may be varied in certain embodiments as would be readily apparent to one of ordinary skill, given the contents of the present disclosure. As used herein, robot 102 may be representative at least in part of any robot described in this disclosure.

Controller 118 may control the various operations performed by robot 102. Controller 118 may include and/or comprise one or more processing devices 138 (e.g., microprocessing devices) illustrated in FIG. 1B, and other peripherals. As previously mentioned and used herein, processing device, microprocessing device, and/or digital processing device may include any type of digital processing device such as, without limitation, digital signal processing devices ("DSPs"), reduced instruction set computers ("RISC"), complex instruction set computers ("CISC"), microprocessing devices, gate arrays (e.g., field programmable gate arrays ("FPGAs")), programmable logic device ("PLDs"), reconfigurable computer fabrics ("RCFs"), array processing devices, secure microprocessing devices and application-specific integrated circuits ("ASICs"). Peripherals may include hardware accelerators configured to perform a specific function using hardware elements such as, without limitation, encryption/description hardware, algebraic processing devices (e.g., tensor processing units, quadratic problem solvers, multipliers, etc.), data compressors, encoders, arithmetic logic units ("ALU"), and the like. Such digital processing devices may be contained on a single unitary integrated circuit die, or distributed across multiple components.

Controller 118 may be operatively and/or communicatively coupled to memory 120. Memory 120 may include any type of integrated circuit or other storage device configured to store digital data including, without limitation, read-only memory ("ROM"), random access memory ("RAM"), non-volatile random access memory ("NVRAM"), programmable read-only memory ("PROM"), electrically erasable programmable read-only memory ("EEPROM"), dynamic random-access memory ("DRAM"), Mobile DRAM, synchronous DRAM ("SDRAM"), double data rate SDRAM ("DDR/2 SDRAM"), extended data output ("EDO") RAM, fast page mode RAM ("FPM"), reduced latency DRAM ("RLDRAM"), static RAM ("SRAM"), flash memory (e.g., NAND/NOR), memristor memory, pseudostatic RAM ("PSRAM"), etc. Memory 120 may provide computer-readable instructions and data to controller 118. For example, memory 120 may be a non-transitory, computer-readable storage apparatus and/or medium having a plurality of instructions stored thereon, the instructions being executable by a processing apparatus (e.g., controller 118) to operate robot 102. In some cases, when executed by the processing apparatus, the instructions may be configured to cause the processing apparatus to perform the various methods, features, and/or functionality described in this disclosure. Accordingly, controller 118 may perform logical and/or arithmetic operations based on program instructions stored within memory 120. In some cases, the instructions and/or data of memory 120 may be stored in a combination of hardware, some located locally within robot 102, and some located remote from robot 102 (e.g., in a cloud, server, network, etc.).

It should be readily apparent to one of ordinary skill in the art that a processing device may be internal to or on board robot 102 and/or may be external to robot 102 and be communicatively coupled to controller 118 of robot 102 utilizing communication units 116 wherein the external processing device may receive data from robot 102, process the data, and transmit computer-readable instructions back to controller 118. In at least one non-limiting exemplary embodiment, the processing device may be on a remote server (not shown).

In some exemplary embodiments, memory 120, shown in FIG. 1A, may store a library of sensor data. In some cases, the sensor data may be associated at least in part with objects and/or people. In exemplary embodiments, this library may include sensor data related to objects and/or people in different conditions, such as sensor data related to objects and/or people with different compositions (e.g., materials, reflective properties, molecular makeup, etc.), different lighting conditions, angles, sizes, distances, clarity (e.g., blurred, obstructed/occluded, partially off frame, etc.), colors, surroundings, and/or other conditions. The sensor data in the library may be taken by a sensor (e.g., a sensor of sensor units 114 or any other sensor) and/or generated automatically, such as with a computer program that is configured to generate/simulate (e.g., in a virtual world) library sensor data (e.g., which may generate/simulate these library data entirely digitally and/or beginning from actual sensor data) from different lighting conditions, angles, sizes, distances, clarity (e.g., blurred, obstructed/occluded, partially off frame, etc.), colors, surroundings, and/or other conditions. The number of images in the library may depend at least in part on one or more of the amount of available data, the variability of the surrounding environment in which robot 102 operates, the complexity of objects and/or people, the variability in appearance of objects, physical properties of robots, the characteristics of the sensors, and/or the amount of available storage space (e.g., in the library, memory 120, and/or local or remote storage). In exemplary embodiments, at least a portion of the library may be stored on a network (e.g., cloud, server, distributed network, etc.) and/or may not be stored completely within memory 120. As yet another exemplary embodiment, various robots (e.g., that are commonly associated, such as robots by a common manufacturer, user, network, etc.) may be networked so that data captured by individual robots are collectively shared with other robots. In such a fashion, these robots may be configured to learn and/or share sensor data in order to facilitate the ability to readily detect and/or identify errors and/or assist events.

Still referring to FIG. 1A, operative units 104 may be coupled to controller 118, or any other controller, to perform the various operations described in this disclosure. One, more, or none of the modules in operative units 104 may be included in some embodiments. Throughout this disclosure, reference may be to various controllers and/or processing devices. In some embodiments, a single controller (e.g., controller 118) may serve as the various controllers and/or processing devices described. In other embodiments different controllers and/or processing devices may be used, such as controllers and/or processing devices used particularly for one or more operative units 104. Controller 118 may send and/or receive signals, such as power signals, status signals, data signals, electrical signals, and/or any other desirable signals, including discrete and analog signals to operative units 104. Controller 118 may coordinate and/or manage operative units 104, and/or set timings (e.g., synchronously or asynchronously), turn off/on control power budgets, receive/send network instructions and/or updates, update firmware, send interrogatory signals, receive and/or send statuses, and/or perform any operations for running features of robot 102.

Returning to FIG. 1A, operative units 104 may include various units that perform functions for robot 102. For example, operative units 104 includes at least navigation units 106, actuator units 108, user interface units 112, sensor units 114, and communication units 116. Operative units 104 may also comprise other units such as specifically configured task units (not shown) that provide the various functionality of robot 102. In exemplary embodiments, operative units 104 may be instantiated in software, hardware, or both software and hardware. For example, in some cases, units of operative units 104 may comprise computer-implemented instructions executed by a controller. In exemplary embodiments, units of operative unit 104 may comprise hardcoded logic (e.g., ASICS). In exemplary embodiments, units of operative units 104 may comprise both computer-implemented instructions executed by a controller and hardcoded logic. Where operative units 104 are implemented in part in software, operative units 104 may include units/modules of code configured to provide one or more functionalities.

In exemplary embodiments, navigation units 106 may include systems and methods that may computationally construct and update a map of an environment, localize robot 102 (e.g., find the position) in a map, and navigate robot 102 to/from destinations. The mapping may be performed by imposing data obtained in part by sensor units 114 into a computer-readable map representative at least in part of the environment. In exemplary embodiments, a map of an environment may be uploaded to robot 102 through user interface units 112, uploaded wirelessly or through wired connection, or taught to robot 102 by a user.

In exemplary embodiments, navigation units 106 may include components and/or software configured to provide directional instructions for robot 102 to navigate. Navigation units 106 may process maps, routes, and localization information generated by mapping and localization units, data from sensor units 114, and/or other operative units 104.

Still referring to FIG. 1A, actuator units 108 may include actuators such as electric motors, gas motors, driven magnet systems, solenoid/ratchet systems, piezoelectric systems (e.g., inchworm motors), magneto strictive elements, gesticulation, and/or any way of driving an actuator known in the art. By way of illustration, such actuators may actuate the wheels for robot 102 to navigate a route; navigate around obstacles; rotate cameras and sensors. According to exemplary embodiments, actuator unit 108 may include systems that allow movement of robot 102, such as motorize propulsion. For example, motorized propulsion may move robot 102 in a forward or backward direction, and/or be used at least in part in turning robot 102 (e.g., left, right, and/or any other direction). By way of illustration, actuator unit 108 may control if robot 102 is moving or is stopped and/or allow robot 102 to navigate from one location to another location.

Actuator unit 108 may also include any system used for actuating, in some cases actuating task units to perform tasks, such as actuating dispensing of disinfectant or directing UV lights to selected surfaces. For example, actuator unit 108 may include driven magnet systems, motors/engines (e.g., electric motors, combustion engines, steam engines, and/or any type of motor/engine known in the art), solenoid/ratchet system, piezoelectric system (e.g., an inchworm motor), magnetostrictive elements, gesticulation, and/or any actuator known in the art.

According to exemplary embodiments, sensor units 114 may comprise systems and/or methods that may detect characteristics within and/or around robot 102. Sensor units 114 may comprise a plurality and/or a combination of sensors. Sensor units 114 may include sensors that are internal to robot 102 or external, and/or have components that are partially internal and/or partially external. In some cases, sensor units 114 may include one or more exteroceptive sensors, such as sonars, light detection and ranging ("LiDAR") sensors, radars, lasers, cameras (including video cameras (e.g., red-blue-green ("RBG") cameras, infrared cameras, three-dimensional ("3D") cameras, thermal cameras, etc.), time of flight ("ToF") cameras, structured light cameras, antennas, motion detectors, microphones, and/or any other sensor known in the art. According to some exemplary embodiments, sensor units 114 may collect raw measurements (e.g., currents, voltages, resistances, gate logic, etc.) and/or transformed measurements (e.g., distances, angles, detected points in obstacles, etc.). In some cases, measurements may be aggregated and/or summarized. Sensor units 114 may generate data based at least in part on distance or height measurements. Such data may be stored in data structures, such as matrices, arrays, queues, lists, arrays, stacks, bags, etc.

According to exemplary embodiments, sensor units 114 may include sensors that may measure internal characteristics of robot 102. For example, sensor units 114 may measure temperature, power levels, statuses, and/or any characteristic of robot 102. In some cases, sensor units 114 may be configured to determine the odometry of robot 102. For example, sensor units 114 may include proprioceptive sensors, which may comprise sensors such as accelerometers, inertial measurement units ("IMU"), odometers, gyroscopes, speedometers, cameras (e.g. using visual odometry), clock/timer, and the like. Odometry may facilitate autonomous navigation and/or autonomous actions of robot 102. This odometry may include robot 102's position (e.g., where position may include robot's location, displacement and/or orientation, and may sometimes be interchangeable with the term pose as used herein) relative to the initial location. Such data may be stored in data structures, such as matrices, arrays, queues, lists, arrays, stacks, bags, etc. According to exemplary embodiments, the data structure of the sensor data may be called an image.

According to exemplary embodiments, sensor units 114 may be in part external to the robot 102 and coupled to communications units 116. For example, a security camera within an environment of a robot 102 may provide a controller 118 of the robot 102 with a video feed via wired or wireless communication channel(s). In some instances, sensor units 114 may include sensors configured to detect a presence of an object at a location such as, for example without limitation, a pressure or motion sensor may be disposed at a shopping cart storage location of a grocery store, wherein the controller 118 of the robot 102 may utilize data from the pressure or motion sensor to determine if the robot 102 should retrieve more shopping carts for customers or autonomously apply disinfecting solutions and/or UV lights to shopping carts.

According to exemplary embodiments, user interface units 112 may be configured to enable a user to interact with robot 102. For example, user interface units 112 may include touch panels, buttons, keypads/keyboards, ports (e.g., universal serial bus ("USB"), digital visual interface ("DVI"), Display Port, E-Sata, Firewire, PS/2, Serial, VGA, SCSI, audioport, high-definition multimedia interface ("HDMI"), personal computer memory card international association ("PCMCIA") ports, memory card ports (e.g., secure digital ("SD") and miniSD), and/or ports for computer-readable media), mice, rollerballs, consoles, vibrators, audio transducers, and/or any interface for a user to input and/or receive data and/or commands, whether coupled wirelessly or through wires. Users may interact through voice commands or gestures. User interface units 218 may include a display, such as, without limitation, liquid crystal display ("LCDs"), light-emitting diode ("LED") displays, LED LCD displays, in-plane-switching ("IPS") displays, cathode ray tubes, plasma displays, high definition ("HD") panels, 4K displays, retina displays, organic LED displays, touchscreens, surfaces, canvases, and/or any displays, televisions, monitors, panels, and/or devices known in the art for visual presentation. According to exemplary embodiments user interface units 112 may be positioned on the body of robot 102. According to exemplary embodiments, user interface units 112 may be positioned away from the body of robot 102 but may be communicatively coupled to robot 102 (e.g., via communication units including transmitters, receivers, and/or transceivers) directly or indirectly (e.g., through a network, server, and/or a cloud). According to exemplary embodiments, user interface units 112 may include one or more projections of images on a surface (e.g., the floor) proximally located to the robot, e.g., to provide information to the occupant or to people around the robot. The information could be the direction of future movement of the robot, such as an indication of moving forward, left, right, back, at an angle, and/or any other direction. In some cases, such information may utilize arrows, colors, symbols, etc.

According to exemplary embodiments, communications unit 116 may include one or more receivers, transmitters, and/or transceivers. Communications unit 116 may be configured to send/receive a transmission protocol, such as BLUETOOTH®, ZIGBEE®, Wi-Fi, induction wireless data transmission, radio frequencies, radio transmission, radio-frequency identification ("RFID"), near-field communication ("NFC"), infrared, network interfaces, cellular technologies such as 3G (3GPP/3GPP2), high-speed downlink packet access ("HSDPA"), high-speed uplink packet access ("HSUPA"), time division multiple access ("TDMA"), code division multiple access ("CDMA") (e.g., IS-95A, wideband code division multiple access ("WCDMA"), etc.), frequency hopping spread spectrum ("FHSS"), direct sequence spread spectrum ("DSSS"), global system for mobile communication ("GSM"), Personal Area Network ("PAN") (e.g., PAN/802.15), worldwide interoperability for microwave access ("WiMAX"), 802.20, long term evolution ("LTE") (e.g., LTE/LTE-A), time division LTE ("TD-LTE"), global system for mobile communication ("GSM"), narrowband/frequency-division multiple access ("FDMA"), orthogonal frequency-division multiplexing ("OFDM"), analog cellular, cellular digital packet data ("CDPD"), satellite systems, millimeter wave or microwave systems, acoustic, infrared (e.g., infrared data association ("IrDA")), and/or any other form of wireless data transmission.

Communications unit 116 may also be configured to send/receive signals utilizing a transmission protocol over wired connections, such as any cable that has a signal line and ground. For example, such cables may include Ethernet cables, coaxial cables, Universal Serial Bus ("USB"), FireWire, and/or any connection known in the art. Such protocols may be used by communications unit 116 to communicate to external systems, such as computers, smart phones, tablets, data capture systems, mobile telecommunications networks, clouds, servers, or the like. Communications unit 116 may be configured to send and receive signals comprising of numbers, letters, alphanumeric characters, and/or symbols. In some cases, signals may be encrypted, using algorithms such as 128-bit or 256-bit keys and/or other encryption algorithms complying with standards such as the Advanced Encryption Standard ("AES"), RSA, Data Encryption Standard ("DES"), Triple DES and the like. Communications unit 116 may be configured to send and receive statuses, commands, and other data/information. For example, communications unit 116 may communicate with a user operator to allow the user to control robot 102. Communications unit 116 may communicate with a server/network (e.g., a network) in order to allow robot 102 to send data, statuses, commands, and other communications to the server. The server may also be communicatively coupled to computer(s) and/or device(s) that may be used to monitor and/or control robot 102 remotely. Communications unit 116 may also receive updates (e.g., firmware or data updates), data, statuses, commands, and other communications from a server for robot 102.

In exemplary embodiments, operating system 110 may be configured to manage memory 120, controller 118, power supply 122, modules in operative units 104, and/or any software, hardware, and/or features of robot 102. For example, and without limitation, operating system 110 may include device drivers to manage hardware recourses for robot 102.

In exemplary embodiments, power supply 122 may include one or more batteries including, without limitation, lithium, lithium ion, nickel-cadmium, nickel-metal hydride, nickel-hydrogen, carbon-zinc, silver-oxide, zinc-carbon, zinc-air, mercury oxide, alkaline, or any other type of battery known in the art. Certain batteries may be rechargeable, such as wirelessly (e.g., by resonant circuit and/or a resonant tank circuit) and/or plugging into an external power source. Power supply 122 may also be any supplier of energy, including wall sockets and electronic devices that convert solar, wind, water, nuclear, hydrogen, gasoline, natural gas, fossil fuels, mechanical energy, steam, and/or any power source into electricity.

One or more of the units described with respect to FIG. 1A (including memory 120, controller 118, sensor units 114, user interface unit 112, actuator unit 108, communications unit 116, mapping and localization unit 126, and/or other units) may be integrated onto robot 102, such as in an integrated system. However, according to some exemplary embodiments, one or more of these units may be part of an attachable module. This module may be attached to an existing apparatus to automate so that it behaves as a robot. The module may be detached at a later point in time. Accordingly, the features described in this disclosure with reference to robot 102 may be instantiated in a module that may be attached to an existing apparatus and/or integrated onto robot 102 in an integrated system. After use, the module may be detached from the robot 102 as appreciated by a skilled artisan. Moreover, in some cases, a person having ordinary skill in the art would appreciate from the contents of this disclosure that at least a portion of the features described in this disclosure may also be run remotely, such as in a cloud, network, and/or server.

As used herein, a robot 102, a controller 118, or any other controller, processing device, or robot performing a task, operation or transformation illustrated in the figures below comprises a controller executing computer-readable instructions stored on a non-transitory computer-readable storage apparatus, such as memory 120, as would be appreciated by one skilled in the art.

Figure 1B:
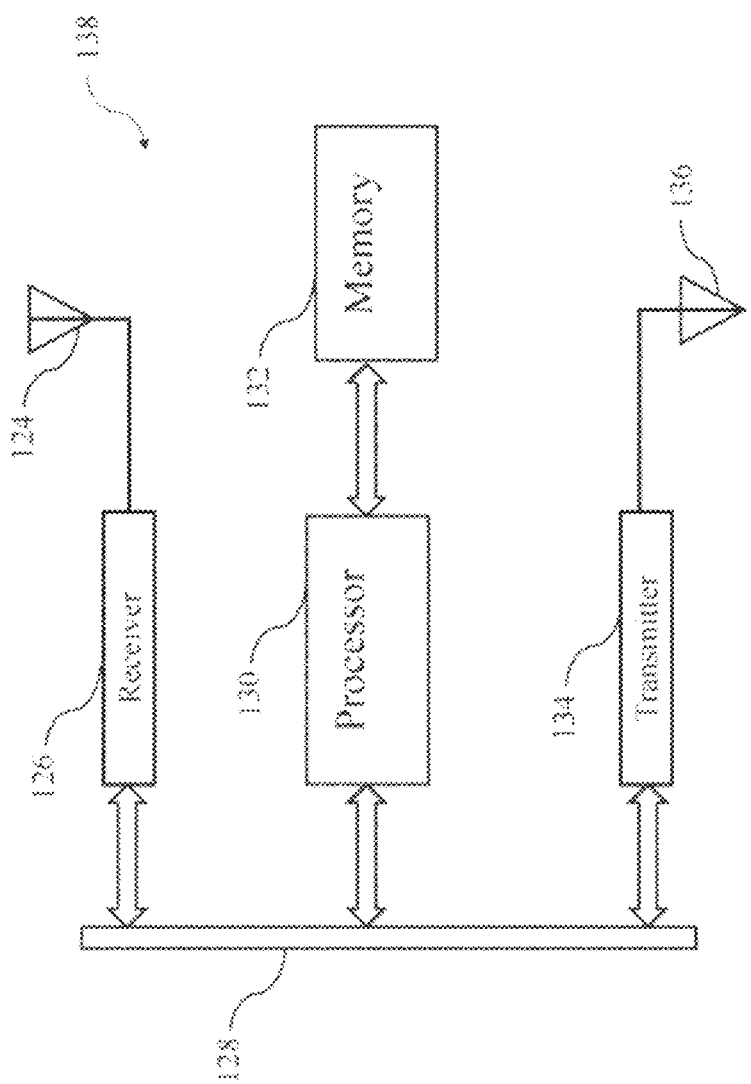
FIG. 1B is a functional block diagram of a controller or processor in accordance with some embodiments of this disclosure.

Next referring to FIG. 1B, the architecture of a processor or processing device 138 is illustrated according to an exemplary embodiment. As illustrated in FIG. 1B, the processing device 138 includes a data bus 128, a receiver 126, a transmitter 134, at least one processor 130, and a memory 132. The receiver 126, the processor 130 and the transmitter 134 all communicate with each other via the data bus 128. The processor 130 is configurable to access the memory 132 which stores computer code or computer-readable instructions in order for the processor 130 to execute the specialized algorithms. As illustrated in FIG. 1B, memory 132 may comprise some, none, different, or all of the features of memory 120 previously illustrated in FIG. 1A. The algorithms executed by the processor 130 are discussed in further detail below. The receiver 126 as shown in FIG. 1B is configurable to receive input signals 124. The input signals 124 may comprise signals from a plurality of operative units 104 illustrated in FIG. 1A including, but not limited to, sensor data from sensor units 114, user inputs, motor feedback, external communication signals (e.g., from a remote server), and/or any other signal from an operative unit 104 requiring further processing. The receiver 126 communicates these received signals to the processor 130 via the data bus 128. As one skilled in the art would appreciate, the data bus 128 is the means of communication between the different components—receiver, processor, and transmitter—in the processing device. The processor 130 executes the algorithms, as discussed below, by accessing specialized computer-readable instructions from the memory 132. Further detailed description as to the processor 130 executing the specialized algorithms in receiving, processing and transmitting of these signals is discussed above with respect to FIG. 1A. The memory 132 is a storage medium for storing computer code or instructions. The storage medium may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage media may include volatile, nonvolatile, dynamic, static, read/write, read-only, random-access, sequential-access, location-addressable, file-addressable, and/or content-addressable devices. The processor 130 may communicate output signals to transmitter 134 via data bus 128 as illustrated. The transmitter 134 may be configurable to further communicate the output signals to a plurality of operative units 104 illustrated by signal output 136.

One of ordinary skill in the art would appreciate that the architecture illustrated in FIG. 1B may illustrate an external server architecture configurable to effectuate the control of a robotic apparatus from a remote location. That is, the server may also include a data bus, a receiver, a transmitter, a processor, and a memory that stores specialized computer-readable instructions thereon.

One of ordinary skill in the art would appreciate that a controller 118 of a robot 102 may include one or more processing devices 138 and may further include other peripheral devices used for processing information, such as ASICS, DPS, proportional-integral-derivative ("PID") controllers, hardware accelerators (e.g., encryption/decryption hardware), and/or other peripherals (e.g., analog to digital converters) described above in FIG. 1A. The other peripheral devices when instantiated in hardware are commonly used within the art to accelerate specific tasks (e.g., multiplication, encryption, etc.) which may alternatively be performed using the system architecture of FIG. 1B. In some instances, peripheral devices are used as a means for intercommunication between the controller 118 and operative units 104 (e.g., digital to analog converters and/or amplifiers for producing actuator signals). Accordingly, as used herein, the controller 118 executing computer-readable instructions to perform a function may include one or more processing devices 138 thereof executing computer-readable instructions and, in some instances, the use of any hardware peripherals known within the art. Controller 118 may be illustrative of various processing devices 138 and peripherals integrated into a single circuit die or distributed to various locations of the robot 102 which receive, process, and output information to/from operative units 104 of the robot 102 to effectuate control of the robot 102 in accordance with instructions stored in a memory 120, 132. For example, controller 118 may include a plurality of processing devices 138 for performing high-level tasks (e.g., planning a route to avoid obstacles) and processing devices 138 for performing low-level tasks (e.g., producing actuator signals in accordance with the route).

Figure 2A:
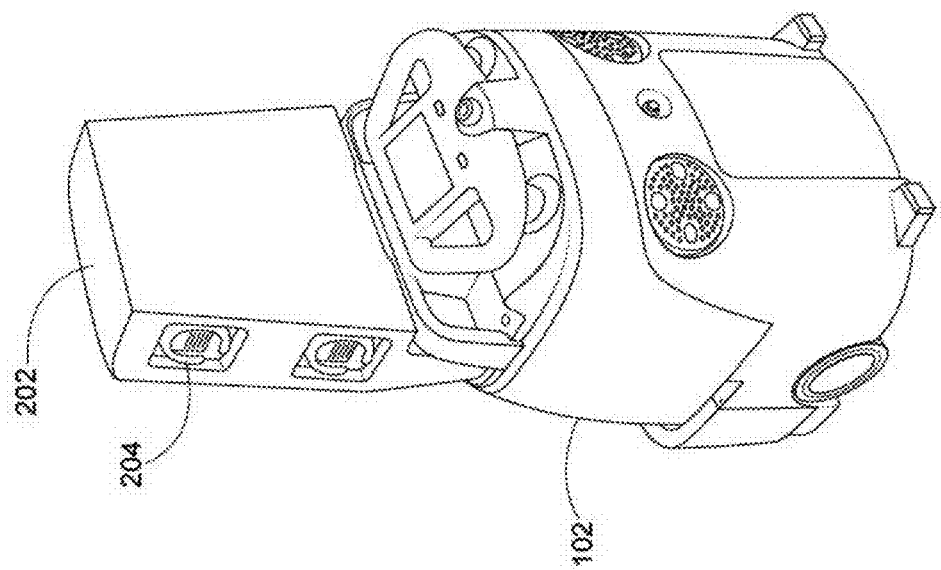

FIG. 2A-B illustrate two perspective views of a robot 102 comprising an ultraviolet ("UV") emission source 202 configured to emit UV light to kill germs, viruses, and bacteria, according to an exemplary embodiment. UV emission source 202 may comprise two UV lights 204 which emit the UV light on both sides of the robot 102 such that, as the robot 102 navigates upon a floor, adjacent objects are disinfected. UV emission sources may emit UV light typically ranging between 200-280 nm, also referred to as UV type C light ("UVC"), or any other wavelength which eliminates germs, viruses, bacteria, and other pathogens. The robot 102 may orient itself, using actuator units 108, such that the fields of view of the UV lights 204 encompass objects or surfaces of which the UV lights 204 are to disinfect.

According to at least one non-limiting exemplary embodiment, UV emission source 202 may be configurable to be modular such that the UV emission source 202 may be coupled/decoupled from the robot 102. For example, robot 102, absent the UV emission source 202, may be configured to perform one or more predetermined tasks, such as cleaning a floor. The UV emission source 202 may be coupled to the robot 102 if an operator of the robot 102 desires the robot 102 to, in addition to cleaning floors, disinfect nearby surfaces. The UV emission source may be coupled to power supply 122 of the robot 102 or may comprise an internal power supply similar to power supply 122 described above in FIG. 1A. In some embodiments, the robot 102 may change its behavior upon detection of the coupled UV emission source 202 module, such as navigating closer to walls or surfaces. In some embodiments, the robot 102 operates in the same manner regardless if UV emission source 202 module is or is not coupled thereto. In some embodiments, the UV emission source 202 comprises some or all of the units described in relation to FIGS. 1A and 1B in an attachable module such that it can perform disinfectant functions described herein attached to an existing apparatus, such as a robot 102, to enhance its capabilities.

Figure 2C:
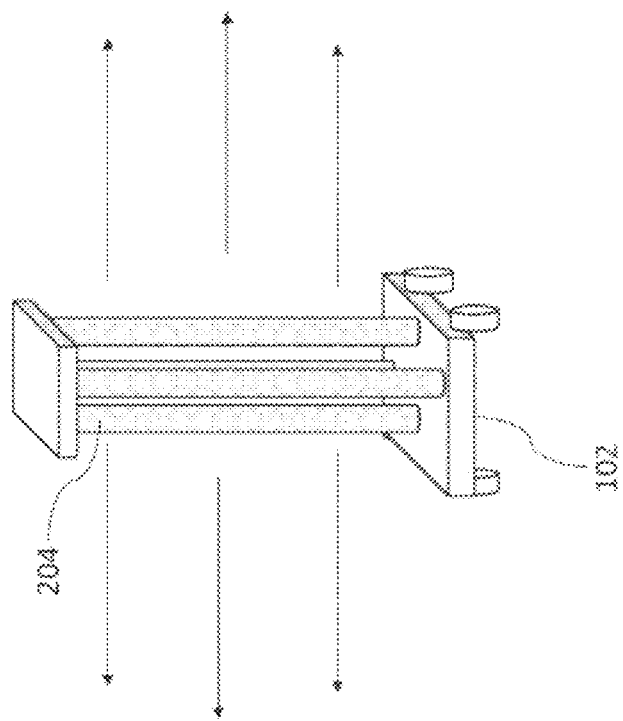

FIG. 2C illustrates another exemplary embodiment of a disinfectant robot 102. The robot 102 may comprise a plurality of cylindrical UV lights 204 configurable to emit UV light in any or plurality of directions (i.e., omnidirectional lights). Four cylindrical lights are shown in the exemplary embodiment shown in FIG. 2C, but the disinfectant robot 102 may comprise, for example, one to ten, or more, UV lights 104. In some instances, a controller 118 of the robot 102 is configurable to utilize constructive and destructive interference (e.g., modulation of the UV light) to amplify/negate UV light within specified regions surrounding the robot 102, thereby enabling directionality of the emitted UV light. The illustrated arrows denote the path followed (i.e., directionality of) UV light emitted by the UV light sources 204 which is configurable using constructive/destructive interference of the four light sources 204. In some embodiments, each of the four UV lights 204 may be directional, wherein actuators 108 of the robot 102 may position or turn the lights 204 to configure the UV light emission pattern in a desired manner, as discussed further below. In some embodiments the controller 118 may configure the UV light pattern in a desired manner by selectively changing the intensity of light emitted by one or more of the UV lights 204, including selectively turning on or off one or more UV lights 204.

Alternatively, a disinfectant robot 102 according to the embodiment shown in FIG. 2C may comprise mechanical devices operated by controller 118 to direct the UV light from directional UV light sources 104 to configure the UV light pattern in a desired manner, such as louvers, shutters, doors, screens, reflectors and the like. Further, a combination of electrical modulation and/or mechanical control of the light emitted from the UV lights 104 may be operated by controller 118 to configure the UV light pattern in a desired manner.

Figure 2D:
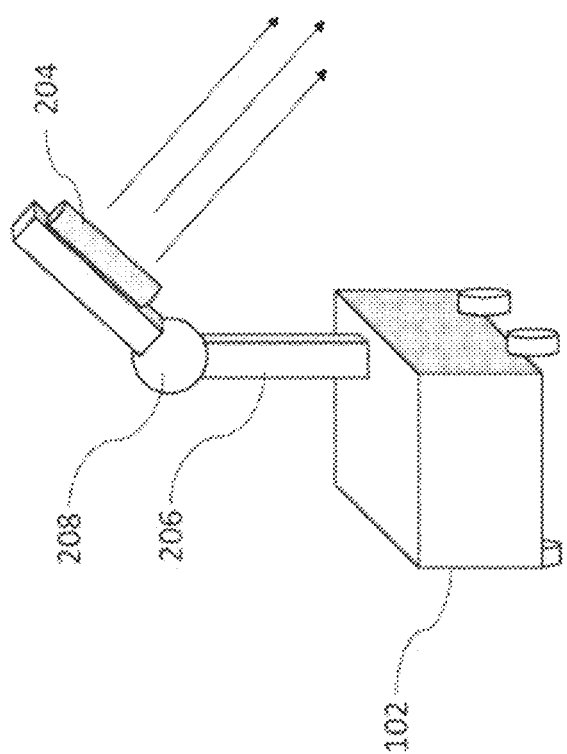

FIG. 2D illustrates another exemplary embodiment of a disinfectant robot 102. The robot 102 may comprise an articulated arm 206 configurable to adjust a position of the UV light source 204. The arm 206 may comprise a joint 208 which may be actuated, via actuators 108, along one to three degrees of freedom. In some instances, the joint 208 is configurable to move in one or two degrees of freedom wherein robot 102 motions may effectuate the remaining degree(s) of freedom. A controller 118 of the robot 102 may utilize actuator units 108 to configure the directionality of the UV light emitted by the UV light source 204 using, e.g., the systems and methods of this disclosure as discussed below. The illustrated arrows denote the path followed (i.e., directionality or emission pattern of) UV light emitted by the UV light sources 204 which is configurable based on the position of the arm 206 and the position of the robot 102.

Figure 2E:
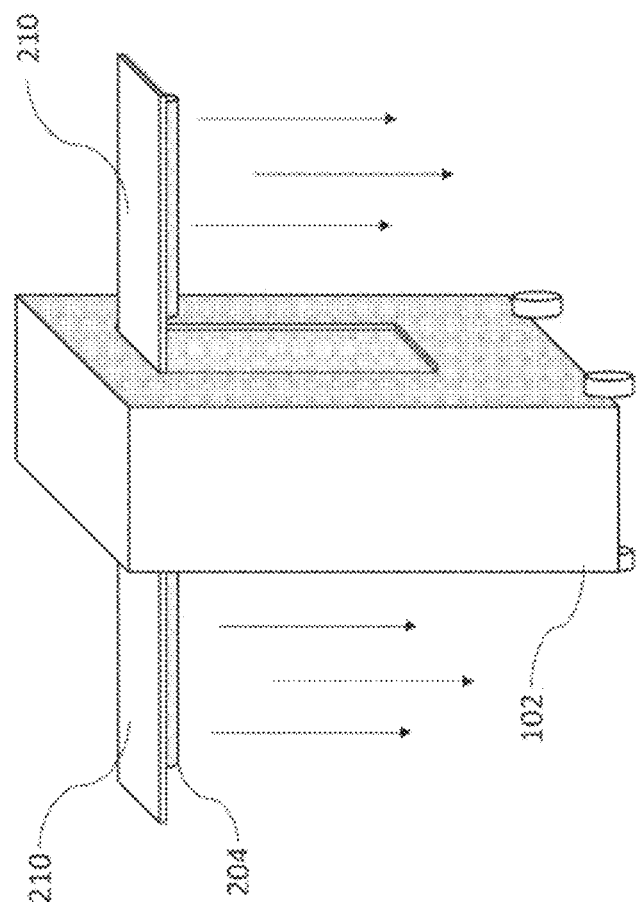

FIG. 2E illustrates another exemplary embodiment of a disinfecting robot 102. The disinfecting robot 102 may comprise a plurality of extendable/retractable features 210 configurable to position UV light sources 204. The exemplary embodiment in FIG. 2E shows two of extendable/retractable features 210. The features 210 may comprise actuated portions of the robot 102 body that extend laterally to the illustrated position when UV light sources 204 are intended to be utilized to disinfect a surface, such as a floor beneath the robot 102, nearby countertops, tables, chairs, and the like. Robot 102 may be sufficiently tall such that features 210 are above most surfaces and the UV light sources 204 emit UV light, shown by arrows, incident upon the surfaces. In some embodiments, features 210 may be coupled to one or more actuator units 108 such that the lights 204 may be oriented along one or more degrees of freedom (e.g., features 210 may rotate to emit UV light ahead, behind, and/or above the robot 102 or may move vertically closer to/farther from the floor). UV light directed above the robot may be useful in disinfecting surfaces on the underside of countertops, tables, chairs, ceilings and the like. The features 210 may be retracted to, for example, avoid objects and to avoid illuminating or disinfecting humans using the systems and methods discussed below.

According to at least one non-limiting exemplary embodiment, the features 210 may include a sensor of sensor units 114 configurable to measure a distance and may be coupled to an actuator 108 to enable vertical positioning of the features 210, for example the distance being measured downwards (i.e., along the direction of the illustrated arrows). The data from the sensors may enable a controller 118 of the robot 102 to position the height of the features 210 at a predetermined distance from a surface of which the UV light is to disinfect. In some embodiments, data from sensors coupled to the robot 102 body may provide the same information used to vertically position the features 210, and thereby vertically position the UV light sources 204 above surfaces.

One skilled in the art may envision a plurality of similar or different robotic bodies comprising one or more UV light source(s) 204 and/or other means for configuring directionality of the light emitted by the light sources 204. The four illustrated embodiments are not intended to be limiting.

Figure 2F:
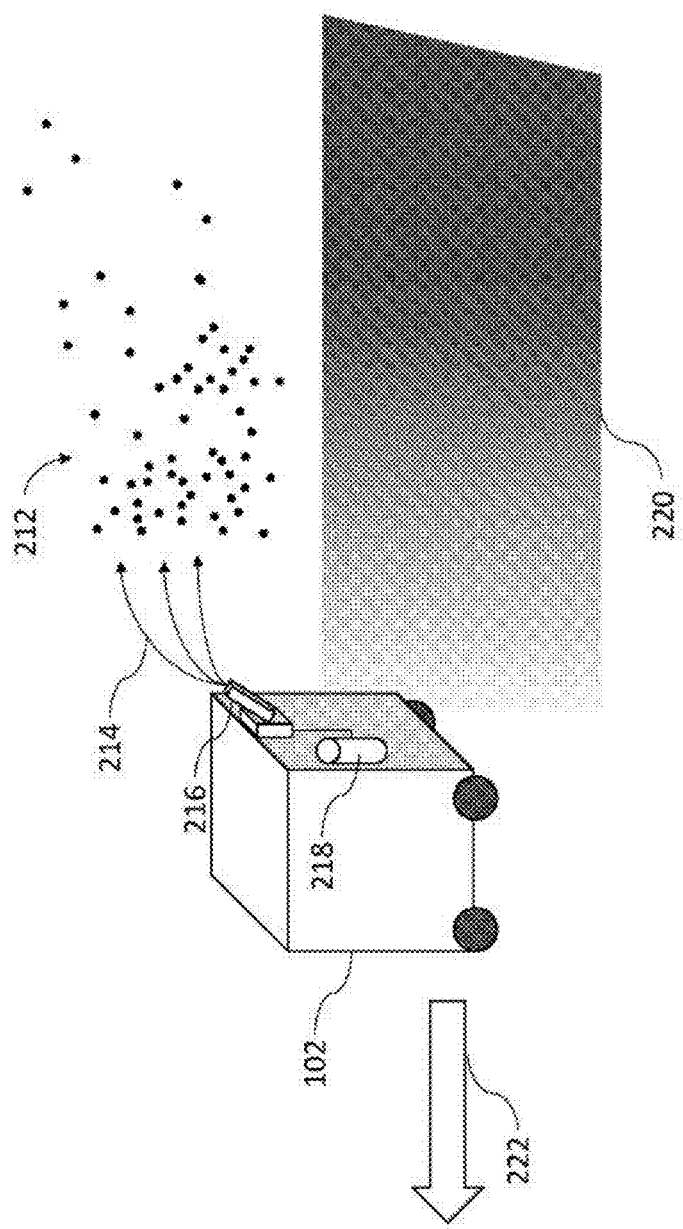
FIG. 2F illustrates a sprayer module configured to emit a disinfecting mist into the environment, according to an exemplary embodiment.

In some embodiments, one or more of the depicted UV light sources 204 depicted in FIG. 2A-E may be replaced with disinfecting sprayers configured to spray disinfecting substances into the environment, in a similar manner as shining the UV light. FIG. 2F illustrates a non-limiting exemplary embodiment of a robot 102 configured to emit a disinfecting spray or mist 212 into the environment. The robot 102 may include a sprayer module 216 coupled to a tank 218 which holds disinfecting liquid, aerosols, or other substances. The substance within the tank 218 may be provided to the sprayer module 216 comprising one or more atomizers and diffusing elements configured to produce a mist 212 of small aerosol particles. Controller 118 of the robot 102 may throttle the substances provided by the tank 218 to the sprayer module 216 in accordance with the systems and methods disclosed below, wherein the robot 102 may avoid spraying nearby humans or within areas where it is not necessary to disinfect (e.g., to reduce usage of the disinfection solution).

The mist 212 emitted from the sprayer module 216 may be sprayed behind the robot 102 as the robot 102 travels through the environment, as shown by arrows 214 and direction of motion 222. This leaves an area 220 behind the robot 102 where mist 212 particles emitted from the sprayer module 216 eventually fall. The area 220 is illustrated using a gradient to illustrate the particles of mist 212 falling onto the floor behind the robot 102, wherein more mist particles 212 land on the floor in area 220 farthest from the robot 102 and area 220 closest to the robot 102 includes most mist particles 212 still being suspended in the air. Although illustrated as a perfect rectangle, area 220 may change due to air currents carrying mist particles 212 to other locations before the mist particles 212 land on a surface. Surfaces of objects within the area 220 may be coated in the disinfection solution as the mist 212 settles, thereby sanitizing the surfaces as the robot 102 moves along direction 222.

The sprayer module 216 and tank 218 may be configured to be modular such that it is able to be coupled to existing robots 102. For example, robot 102 may be a robot configured to perform a specific task, such as cleaning, vacuuming, or sweeping floors; transporting items from one location to another; capture data of its environment, such as maps, images, LiDAR scans, and the like; and/or other robotic use cases which involve the robot 102 moving (e.g., a stationary robotic arm may not benefit substantially from a disinfecting module 216 as its disinfecting area 220 is limited). A modular sprayer module 216 may be coupled to the robot 102 to enable the robot 102 to disinfect the environment in addition to its normal tasks. While the robot 102 performs its normal tasks, sprayer module 216 may emit mist 212 to disinfect the surrounding environment with little modification to the behavior of the robot 102 itself.

Advantageously, a sprayer module 216 configured to be coupled to existing robots 102 enable these robots 102 to expand their use and functionality to disinfect the environment without hindering their performance of other tasks. The controller 118 of the robot 102 may update the footprint of the robot 102 stored in memory 120 to account for the added volume of the sprayer module 216 and tank 218, the footprint corresponds to a digital representation of the area occupied by the robot 102 used by the controller 118 to represent the area occupied and location of the robot 102 in its environment and to detect/avoid collisions. One skilled in the art may appreciate that coupling a sprayer module 216 to an existing robot 102 may further include configuring the sprayer module 216 to comprise an interface to facilitate electromechanical coupling of the sprayer 216 to the robot 102 body, the design of the interface may be specific to the size, shape, and electrical layout (e.g., available ports) of the robot 102 and has been omitted from the drawing for clarity. For example, the interface may include permanent or non-permanent attachment mechanisms such as latches, screws, slots, grooves, glues, etc. which mechanically attach to the robot 102 external chassis. Further, the interface may include one or more wires which couple to the controller 118 of the robot 102 (e.g., via an available access port on a circuit board) or may be wirelessly coupled to the controller 118 via communication units 116 to facilitate the modulation of the emitted mist 212 by the controller 118.

According to at least one non-limiting exemplary embodiment, the sprayer module 216 may be configured to spray mist 212 outwards from one or both sides of the robot 102. That is, the sprayer module 216 spraying mist 212 directly behind the robot 102 is not intended to be limiting. Sprayer 216 may spray mist ahead of the robot 102 along direction 222; however, disinfecting chemicals may often build up and damage the robot 102 and/or sensors 114 if the robot 102 is continuously driving into the mist 212.

According to at least one non-limiting exemplary embodiment, multiple sprayer modules 216 may be affixed to a robot 102. For example, three sprayers 216 may be coupled to the robot 102 to spray mist 212 along the left side, right side, and rear of the robot 102. Multiple sprayers 216 may utilize a shared tank 218 or separate tanks 218 to store disinfecting solution.

According to at least one non-limiting exemplary embodiment, the sprayer module 216 may be coupled to the controller 118 of the robot 102 wirelessly or via wired connection. Robots 102 disclosed herein may learn routes and tasks by following a user demonstration, wherein a human may manually move/drive the robot 102 along a route causing the robot 102 to record its motion to autonomously recreate the route. While training the robot 102, the human may activate/deactivate the sprayer module 216 to teach the robot 102 where the sprayer module 216 should be activated or deactivated. While in the training or learning mode, the input to activate the sprayer 216 may be received and recorded, but the mist 212 may not be emitted to avoid spraying the human trainer. In addition to the learned locations to emit the mist 218, the controller 118 may further modulate the emission of mist 212 to avoid disinfection when it may disturb nearby humans using methods disclosed below.

According to at least one non-limiting exemplary embodiment, the sprayer module 216 may not be coupled to the controller 118 of the robot 102 and operate using its own separate controller, microprocessor, or processor. The sprayer module 216 in this embodiment may further include buttons, switches, and/or other devices configured to receive a user input to activate or deactivate the emission of mist 212 manually.

Figure 3A:
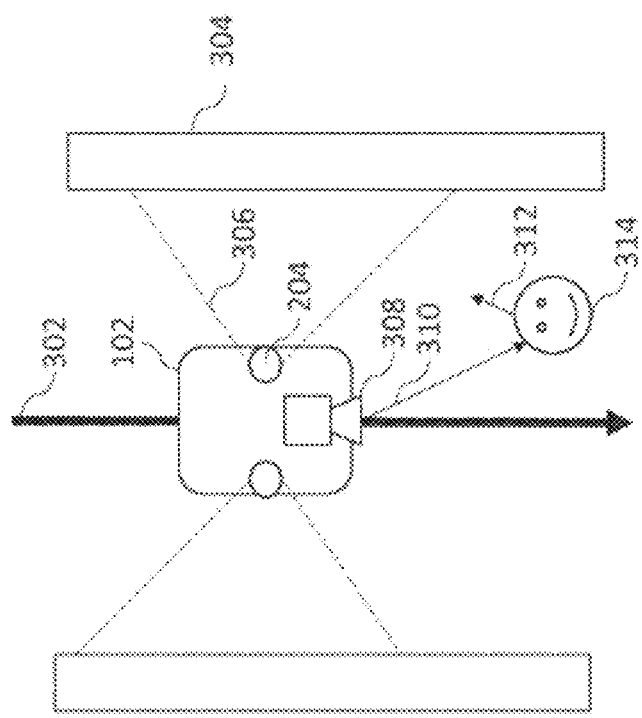

FIG. 3A illustrates a robot 102 navigating a route 302 and utilizing UV lights 204 to disinfect surfaces of objects 304, according to an exemplary embodiment. Objects 304 may include tables, chairs, desks, walls, shelves (e.g., grocery store shelves), vehicles, doors, and/or any other object which is able to be illuminated with UV light (200-280 nm) without damage. For simplicity of illustration, the robot 102 in FIG. 3A may include two UV lights 204 disposed on its left and right sides, the UV lights 204 include a field of view illustrated by lines 306. However one skilled in the art may appreciate that UV lights 204 may be disposed on the robot 102 in any location, comprise any field of view, and may be fewer or greater in number than the illustrated exemplary embodiment.

As the robot 102 navigates the path 302, a sensor 308 of sensor units 112 may detect a nearby human 314 as shown by arrow 310. It may be dangerous or undesirable for a human 314 to be illuminated with UV light as the UV light may cause skin damage, be bright/uncomfortable, and/or cause unnecessary tanning. In some embodiments, sensor 308 may be illustrative of two or more exteroceptive sensor units 114. The controller 118 of the robot 102 may determine the presence of a human based on, for example, motion detection and/or extracting landmarks, or features, from known landmarks or features of a human such as facial recognition, body language recognition, thermal imaging information, facial expression recognition, and/or audible (e.g., voice) recognition. The controller 118 of the robot 102 may determine a motion vector 312 of the human based on, for example, sequential images captured by the sensor 308 (e.g., sensor 308 being an image camera), temporal change in measured distance to the human (e.g., sensor 308 being a depth camera or LiDAR), motion tracking (e.g., sensor 308 being a motion tracking sensor), or other conventional method (e.g., salient object perception, gait pattern detection, etc.). The controller 118 may utilize, for example, image recognition methods (e.g., convolutional neural network models, predetermined filters, etc.) or gait pattern recognition methods (e.g., using LiDAR point cloud data) to identify that the object 314 is a human.

Upon identifying the human 314 is approaching the robot 102, the controller 118 may adjust the directionality of the UV light emitted by light sources 204 as shown next in FIG. 3B, according to a non-limiting exemplary embodiment. As shown, the left light source 204 comprises a different emission pattern, directionality, or field of view than the right light source 204, illustrated by lines 306. The configuration of the different emission pattern may be configured based on the motion vector 312 which denotes the predicted path traveled by the human 314. The predicted path may be based on prior motions of the human (e.g., as shown in FIG. 3A wherein the human 314 approaches the left side (right side on the illustration) of the robot 102). The controller 118 of the robot 102 may configure the emission pattern of the left light source 204 (right side of the illustration) such that the emission pattern does not illuminate the human 314. The emission pattern may be changed using, for example, one or more actuator units 108 to change a position of the UV light source 204 or constructive/destructive interference of UV light. As the robot 102 continues along the route 302, other sensor units 114 (not shown) may continue to detect the human 314 nearby the robot 102 until the human 314 is far from the robot 102, wherein the controller 118 may resume emitting UV light in the pattern shown in FIG. 3A.

According to at least one non-limiting exemplary embodiment, upon detecting a human 314, the controller 118 may disable one or both UV lights 204 until the human is a threshold distance away from the robot 102. Due to UV light being invisible to humans, humans may be apprehensive to approach the robot 102 when UV lights 204 are activated. In some instances, the robot 102 may stop navigation along route 302 until the human 314 has passed, wherein the UV lights 204 may be reenabled. The robot 102 may further comprise a visual and/or audible indicator, e.g. such as one or more visible lights, that inform a human that the UV lights are activated and/or the directionality of UV lights emitted by the UV emission source 202.

According to at least one non-limiting exemplary embodiment, the emission pattern of the UV light sources 204 may be configured based on the presence, or lack thereof, of nearby objects which are to be disinfected. For example, if an object 304 is only present on one side of the robot 102, only the UV light source 204 on the same side may be active. As another example, the object 304 may be of a certain size and shape, wherein the emission patterns of UV light shown by lines 306 may be configured based on the size and shape of the object 304 such that only the object 304 is illuminated with UV light and surrounding objects (e.g., humans 314) are not illuminated. The emission pattern may change over time as the robot 102 moves.

According to at least one non-limiting exemplary embodiment, the controller 118 may disable or modify the emission of UV light, or a portion thereof, upon detecting any moving object approaching the robot 102 (e.g., object 314 may be other than a human such as a pet or farm animal).

According to at least one non-limiting exemplary embodiment, robot 102 may halt navigation along route 302 upon detecting the human 314 and disable or modify the emission pattern of the UV light. The robot 102 may continue navigation upon the human 314 moving a threshold distance from the robot 102 or moving beyond the emission pattern 306 such that the robot 102 disinfects the entire surface of objects 304.

According to at least one non-limiting exemplary embodiment, the robot 102 may utilize a computer-readable map to navigate about its environment, wherein objects comprising glass or reflective surfaces (e.g., mirrors, metallic walls, glossy white walls, etc.) may be localized onto the map. The controller 118 of the robot 102 may change or disable the emission pattern of UV light to avoid illuminating the reflective or glass surfaces as reflected UV light may be dangerous or damaging to nearby humans, robots, and objects.

According to at least one non-limiting exemplary embodiment, the fields of view shown by lines 306 may be smaller or larger than illustrated. In some instances, the lines 306 may be parallel and extend laterally from the robot 102 such that the UV light emitted by light sources 204 is highly directional and focused to a line or point on the surfaces of the objects 304, wherein motion of the robot 102 along route 302 may enable the UV light to disinfect the surface of objects 304 (i.e., sweep across the surface as the robot 102 moves).

Advantageously, the controller 118 utilizing sensor unit 114 data to localize a human 314 and adjust the emission pattern of the UV light may improve safety of operating disinfecting robots 102 in environments comprising humans. For example, objects 304 may be illustrative of shelves in a grocery store, wherein robot 102 may pass by store workers and/or shoppers (314) as it disinfects the items on the shelves. Adjusting or configuring the emission pattern of UV light in response to sensor units 114 detecting a human 314 may enable the robot 102 to disinfect objects 304 within crowded environment while posing no risk to nearby humans 314.

In some embodiments of robot 102, robot 102 may be configurable to learn or follow a path which is stored in memory 120 or received via communications (e.g., from an external server). The paths may be learned via the robot 102 navigating the paths in a training mode or via an operator creating the path. Disinfecting robots 102 have applications in hospitals, wherein the absence of pathogens is critical to patient health. Accordingly, it may be advantageous for a disinfecting robot 102 to navigate within a plurality of patient rooms, wherein occupied rooms may require the robot 102 to follow a different path than unoccupied rooms to avoid illuminating the human occupancy with UV light. Training of separate routes for occupied and unoccupied rooms may take a substantial amount of time from operators of the robots 102. The systems and methods of the present disclosure, however, may enable a disinfecting robot 102 to navigate a same path through a patient room whether or not the patient is present.

Figure 4:
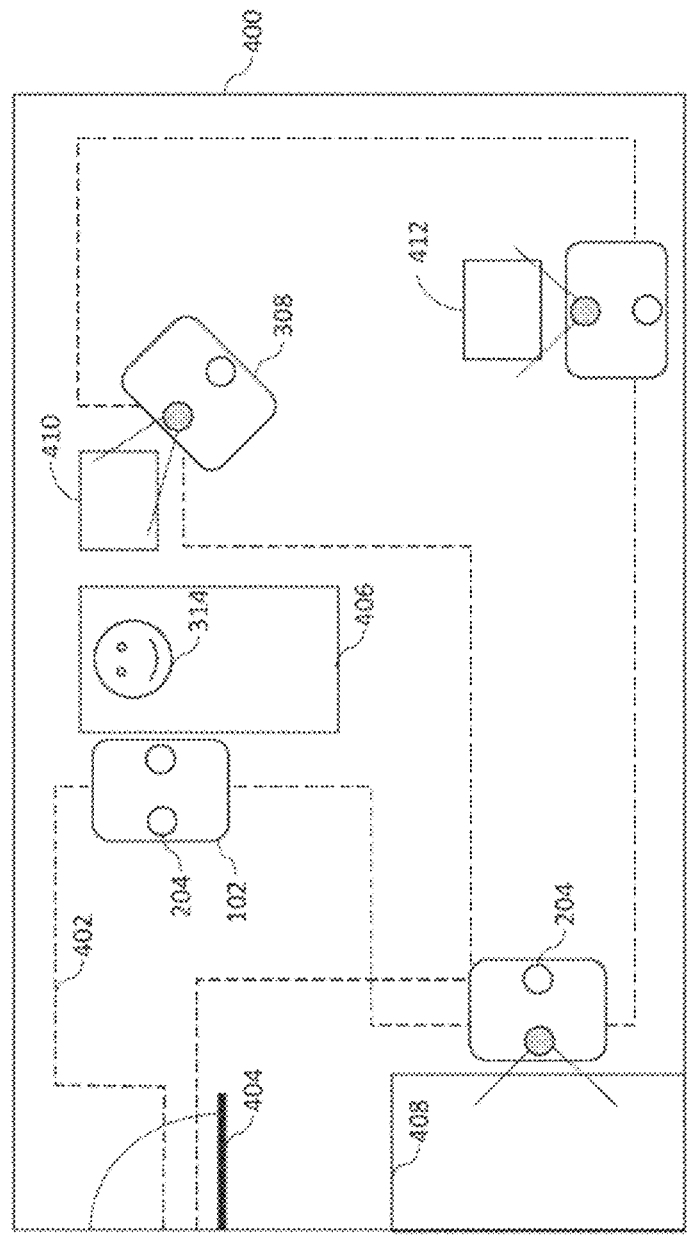
FIG. 4 illustrates a robot sanitizing a room comprising a human resident, according to an exemplary embodiment.

FIG. 4 illustrates a robot 102 following a path 402 through a patient room 400 within a hospital, according to an exemplary embodiment. The path 402 may configure the robot 102 to enter the room 400 via a door 404 and navigate to nearby surfaces 406, 408, 410, 412 to utilize UV light sources 204 to disinfect the surfaces. As shown, a human 314 may occupy a bed 406 which, absent the human 314, the memory 120 of the robot 102 comprises instructions which configures the robot 102 to disinfect the bed 406 using the UV light sources 204 in addition to the various other surfaces 408, 410, 412 within the room 400. In some instances, the robot 102 may further disinfect the floor using UV light sources 204 or a disinfecting cleaner.

A controller 118 of the robot 102 may utilize data from one or more sensor units 114 to detect the human 314 in the bed 406. Accordingly, the controller 118 may skip disinfection of the bed 406 and may continue along the route 402 to disinfect the other surfaces 408, 410, 412 of the room. The robot 102 is illustrated in four locations within the room 400, wherein each location illustrates the robot 102 disinfecting a surface 408, 410, 412, except for the bed 406 due to the human 314 occupant being present. The light source 204 illustrated in grey denotes a UV light source 204 which is enabled (i.e., emitting UV light) to disinfect a nearby surface 408, 410, 412. As shown, the controller 118 may utilize position and location data of the robot 102 (e.g., from navigation units 106) within the room 400 to determine which light source 204 is to be enabled and/or how to configure the directionality of the emission pattern. Advantageously, the robot 102 is able to disinfect the hospital room 400 using a predetermined route 402 regardless of the presence of the human 314, wherein absent the human 314 the robot 102 may also disinfect the bed 406.

In some instances, the human may be moving about the room 400 or there may be multiple humans visiting the illustrated human 314 moving about the room. Robot 102 may still execute path 402 and configure the emission of UV lights to avoid the humans, as shown above in FIG. 3A-B. Alternatively, the controller 118 of the robot 102 may determine that disinfecting one or more of the surfaces 406, 408, 410, 412 in room 104 may be impractical or undesirable in the presence of humans 314 and determine that the robot will return to room 400 at a later time (e.g., if the humans obstruct the robot 102 from disinfecting a threshold amount of surfaces 406, 408, 410, 412 or square footage). The controller 118 of the robot 102 may track which surfaces 406, 408, 410, 412 have been disinfected for a later determination as to when the robot 102 should revisit the room 400, as discussed further in FIG. 7-8 below.

According to at least one non-limiting exemplary embodiment, the room 400 may be a hotel room, wherein the robot 102 comprises an automated housekeeping robot. In some instances, the human 314 may work alongside the robot 102 within the hotel (e.g., human 314 being a house keeping associate making the bed 406), wherein the robot 102 may execute route 402 to disinfect the surfaces, 406, 408, 410, 412 while avoiding illuminating the human 314 (e.g., may skip disinfecting the bed 406 while the human 314 is nearby and, later, disinfect the bed 406 when the human 314 is elsewhere). That is, room 400 being within a hospital is purely illustrative and not intended to be limiting. Further, the term "room" is not limited to a single enclosed space. For example, the term "room" may include an enclosed space comprising one or more of a sleeping section, a bathroom section, seating section and a food preparation and consumption section (e.g. kitchen), wherein one or more sections may or may not be separately enclosed from the other sections. For example, as used herein, the term "room" may also include enclosures for human or animal habitation including dormitories, bunkrooms, temporary shelters, suites, apartments, stables, barns, kennels, poultry houses and the like that may require disinfection.

Advantageously, by configuring the controller 118 to detect humans within images captured by sensor unit 114 data, the robot 102 is able to disinfect a room (e.g., 400) while humans are within the room. For example, the disinfectant robot 102 may clean a room 400 within a hospital in conjunction with a human worker to enhance the rate at which hospital rooms are prepared for a new patient (or hotel rooms for a new guest, etc.). Further, by directing the emission patterns of the UV light towards surfaces 406, 408, 410, 412, the power consumed by the UV lights 204 is greatly reduced. Although the human occupant 314 reduces the amount of disinfection performed within the room 400, no personal protective equipment ("PPE") nor human workers are required to provide at least some disinfection to the room 400. Further, the robot 102 may revisit the room 400 following the methods illustrated in FIG. 7-8 below. Alternatively, the robot 102 may be configurable to perform disinfecting actions sequentially to (i.e. before or after) actions performed by a human 314 to optimize efficiency of room turnover by timing operations when for example, the human may be in another section of the room performing a task. For illustration, a robot 102 may disinfect the surfaces in a bathroom section while a human is performing a task in the sleeping section such as making a bed.

Figure 5:
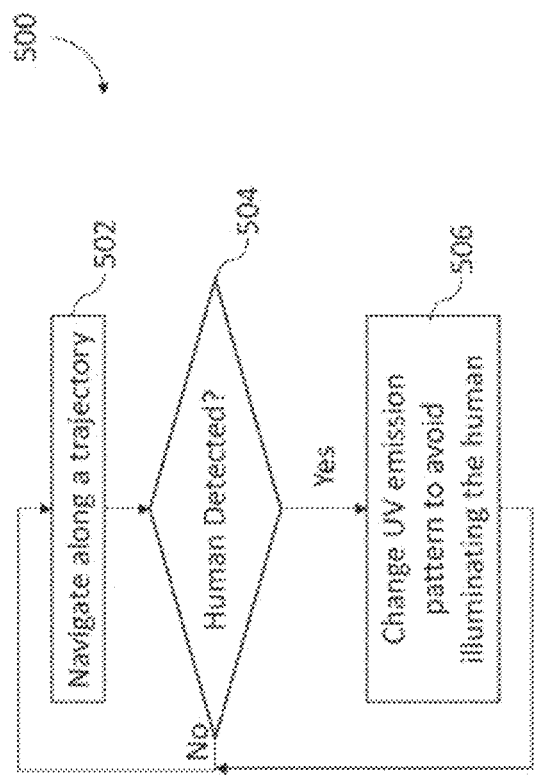
FIG. 5 is a process flow diagram illustrating a method for a controller of a robot to configure emission of ultraviolet light, according to an exemplary embodiment.

FIG. 5 is a process flow diagram illustrating a method 500 for a disinfecting robot 102, comprising at least one UV light source 204 to operate nearby humans, according to an exemplary embodiment. Steps of method 500 may be effectuated via a processing device 138 of the controller 118 executing computer-readable instructions from a computer-readable memory.

Block 502 includes the controller 118 navigating the robot 102 along a trajectory. The trajectory may be in accordance with a predetermined route (e.g., 302, 402), following an object (including a human), navigating to a specified location, and/or any other trajectory. As the robot 102 navigates the trajectory, the controller 118 may configure one or more UV light sources 204 to emit UV light incident upon surfaces to disinfect the surfaces.

Block 504 includes the controller 118 determining if data from sensor units 114 detects a human proximate the robot 102. In some embodiments, sensor units 114 may capture images (e.g., RGB, YUV, HSV, greyscale, etc. images) of a visual scene surrounding the robot 102. The controller 118 may utilize computer vision algorithms (e.g., convolutional neural networks, Gabor filters, etc.) to identify humans within the images. In some embodiments, gait pattern recognition may be utilized to identify humans in LiDAR scan data or depth images. In some embodiments, a "human" may correspond to any object near the robot 102 which moves. In some embodiments, the controller 118 may compare data from the sensor units 114 with one or more libraries of data comprising measurements of humans, wherein a similarity between data from the sensor units 114 and the libraries may correspond to detection of a human. One skilled in the art may appreciate that the use of any contemporary human detection algorithm is applicable based on the specific sensor units 114 of the robot 102.

Upon the controller 118 determining there is no human is proximate the robot 102, the controller 118 returns to block 502 to continue navigation along the route.

Upon the controller 118 determining there is one or more human(s) proximate the robot 102, the controller 118 moves to block 506.

Block 506 includes the controller 118 changing the UV emission pattern of the one or more UV light sources 204 such that the emission pattern does not illuminate the human with UV light. In some embodiments, a robot 102 may orient itself in a way such that the UV light is not incident upon the human. In some embodiments, the controller 118 may modulate the UV light to utilize constructive/destructive interference to change the emission pattern. In some embodiments, the controller 118 may actuate one or more actuator units 108 (e.g., actuators of joint 208 shown in FIG. 2D) to change the emission pattern by moving the UV light source 204. In some embodiments, the controller 118 may disable one or more of the UV light sources 204 upon detecting the human. The controller 118 may return to block 502 upon the human moving away from the robot 102 beyond the range of the UV light sources 204. In some embodiments, the robot 102 may halt (i.e., stop) navigation upon detection of the human until the human has moved away from the robot 102 prior to returning to block 502.

According to at least one non-limiting exemplary embodiment, a robot 102 may include UV light sources 204 for disinfecting surfaces and may further include other sources of disinfectant, such as sprays, liquids, or other solutions. It may be desirable to spray some surfaces with disinfectant while illuminating other surfaces with UV light. For example, if a robot 102 operates within a grocery store, it may be advantageous to illuminate produce with UV light while spraying other objects which may be sensitive to high intensity UV light (e.g., lighter fluids, cosmetics, cleaners, etc.) with a disinfectant spray.

Figure 6A:
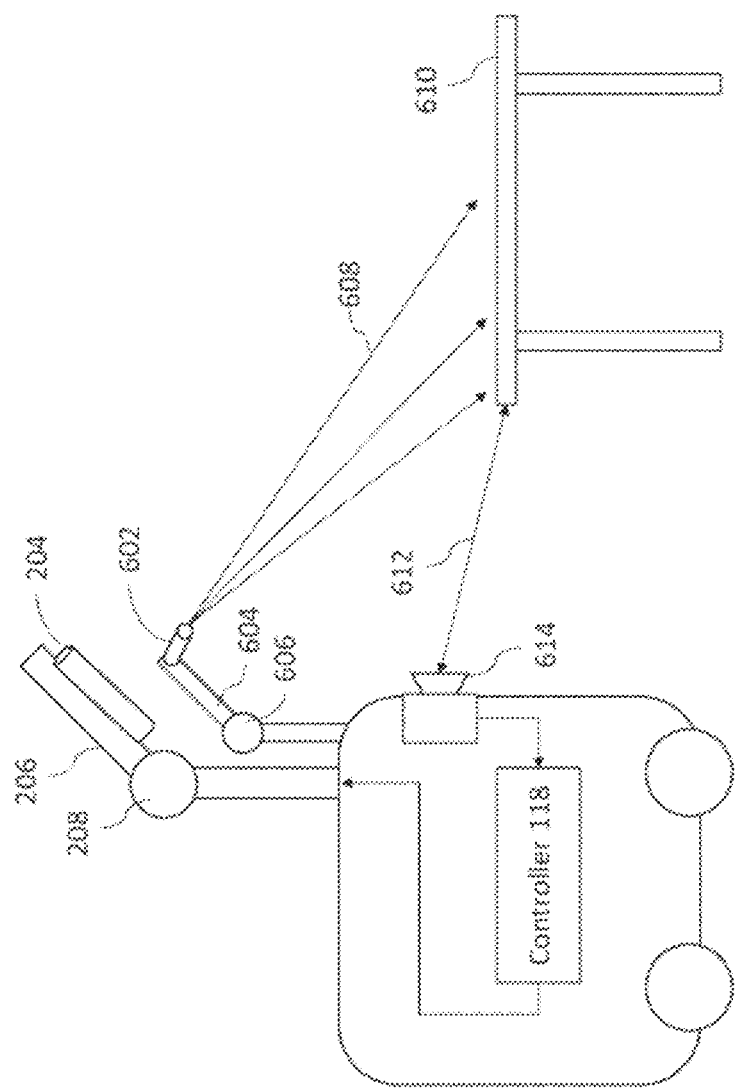
FIG. 6A illustrates a robot disinfecting a surface of a table using a disinfectant spray, according to an exemplary embodiment.

FIG. 6A illustrates a robot 102 comprising both a UV light source 204, coupled to an articulated arm 206 previously shown in FIG. 2D, and a disinfectant sprayer 602 coupled to an articulated arm 604 similar to arm 206 shown in FIG. 2D, according to an exemplary embodiment. Arm 604 may include a joint 606 or mechanical means which enables movement of the sprayer 602 along one or more degrees of freedom. Sprayer 602 may comprise a nozzle coupled to one or more reservoirs or tanks of disinfectant spray stored within the robot 102 body. It may be appreciated that any other embodiment of a UV emission source such as those shown in FIGS. 2A-E or any combination of embodiments of UV emission sources may also be contemplated in the embodiments related to FIGS. 6A-6C. It may also be appreciated that a single articulated arm 604 may comprise both UV light source 204 and a disinfectant sprayer 602, as described further below.

Robot 102 may include a sensor 614 of exteroceptive sensor units 114 configured to capture images of an environment surrounding the robot 102. The sensor 614 may capture images encoded with RGB, greyscale, HSV, YUV, or other color formats. Sensor 614 may capture images which depict, at least in part, the table 610 as shown by arrow 612. A controller 118 of the robot 102 may utilize data from the sensor 614 and/or other sensor units 114 to determine if the table 610 is to be illuminated with UV light, sprayed with a disinfectant, or both. The controller 118 may determine the object is a table 610 using predetermined filters, convolutional neural network models, libraries of data, computer-readable maps, and the like. Controller 118 may embody a lookup table or other model (e.g., one derived from a convolutional neural network) stored in memory 120 which enables the robot 102 to determine which method of disinfection it should use to disinfect the surface of table 610. In the illustrated embodiment, the robot 102 may utilize the sprayer 602 to spray a disinfectant upon the surface of table 610 as shown by arrows 608. The controller 118 may actuate a feature of the robot 102, such as arm 604 and joint 606, to position the nozzle of the sprayer 602 such that the disinfectant is incident upon the table 610, the position of the nozzle being based on data from sensor 614 and/or other sensor units 114.

According to at least one non-limiting exemplary embodiment, the memory 120 may store a computer-readable map of the environment of the robot 102, wherein table 610 may be localized and identified based on the computer-readable map and the position of the robot 102.

According to at least one non-limiting exemplary embodiment, both the sprayer 602 and UV light source 204 may be configured on the same arm (e.g., 206, 604) or other mechanical means for positioning the sprayer 602 and UV light source 204. The mechanical means may include, in part, the position and orientation of the robot 102 (e.g., the robot 102 may position itself to aim the UV light source 204 or sprayer 602 towards the table 610), wherein the positions of the UV light source 204 and sprayer 602 on the robot 102 may be fixed. In some embodiments, the mechanical means for positioning the UV light source 204 and sprayer 602 may include extending or retracting the UV light source 204 and/or sprayer 602 from within the robot 102 body (e.g., as similarly shown in FIG. 2E). Other similar mechanical means for positioning the sprayer 602 and UV light source 204 may be envisioned by one skilled in the art, wherein the use of arms 206, 604 is indented to illustrate the broader inventive concepts of this disclosure.

Figure 6B:
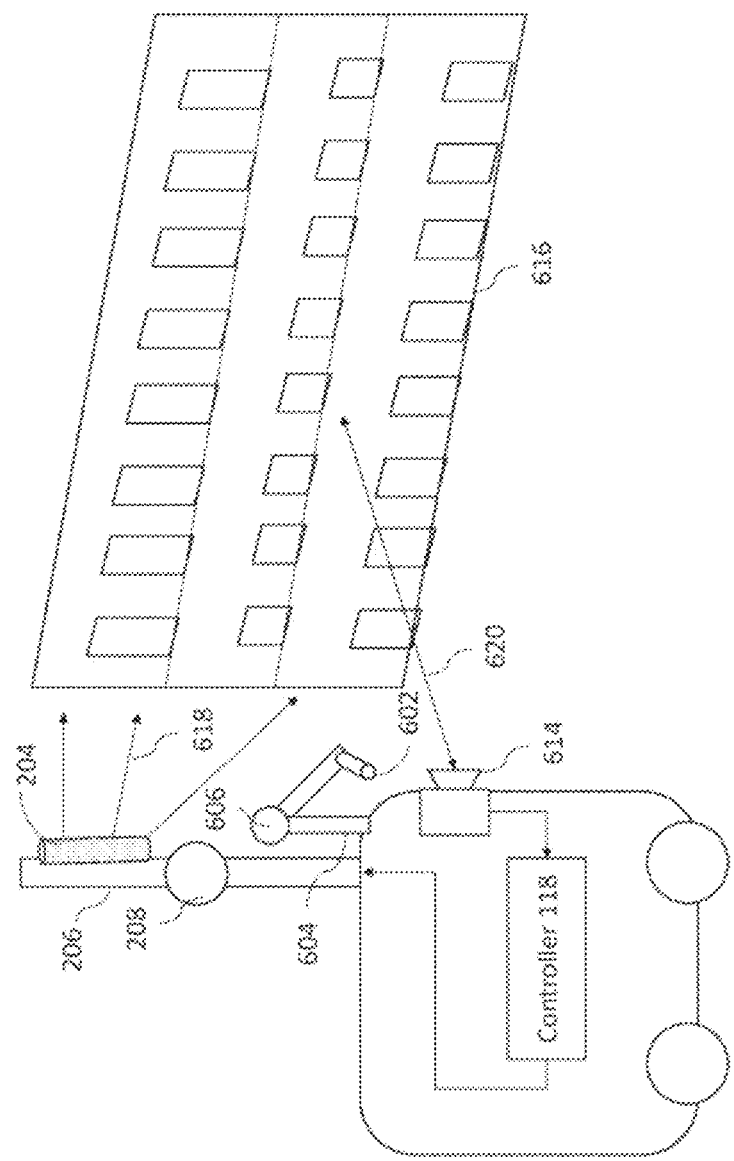
FIG. 6B illustrates a data table used by a robot to determine which method of disinfection should be used for various objects within its environment, according to an exemplary embodiment.

Next, in FIG. 6B, the same robot 102 shown in FIG. 6A navigates nearby and detects a shelf 616 using sensor 614, the shelf 616 includes a plurality of items, according to an exemplary embodiment. It may be undesirable for the items on the shelf 616 to be sprayed with disinfectant as the items may become damaged or undesirable to customers. Accordingly, the controller 118 may utilize the UV light source 204 to disinfect the shelf 616, shown by arrows 618. The controller 118 may utilize the same model or lookup table used to identify the table 610, shown in FIG. 6A, and determine the table 610 was to be sprayed with disinfectant. The robot 102 may continue to disinfect the shelf 616 unless or until a human is detected within close proximity to the robot 102 using sensor 614 and/or other sensor unit 114 of the robot 102, wherein the robot 102 may utilize any of the systems and methods of the present disclosure to direct the UV light away from the detected location of the human as shown in FIG. 3-4 above.

FIG. 6C illustrates a lookup table 622 stored in a memory 120 of a robot 102 for use by the robot 102 to determine which objects/surfaces should be disinfected using a disinfectant spray or UV light, according to an exemplary embodiment. Entries of the lookup table 622 may be preprogrammed by a manufacturer of the robot 102 or configured by an operator of the robot 102 via user interface units 112. For example, the user interface units 112 may include a visual display (e.g., a touch screen tablet, computer monitor, etc.) which lists a plurality of items and surfaces, wherein an operator may provide input to the user interface units 112 corresponding to a desired disinfecting action the robot 102 should take upon detecting the listed objects. For example, the table 622 may denote that tables and floors should be sprayed with disinfectant while beds, shelves, and walls should be illuminated with UV light. One skilled in the art may appreciate that data table 622 may be a self-referential data table wherein additional rows may be added as the controller 118 executes computer-readable instructions from memory 120 and/or receives additional user input from user interface units 112.

According to at least one non-limiting exemplary embodiment, data table 622 may illustrate inputs and outputs of an image recognition model embodied by controller 118 executing computer-readable instructions from memory 120. The image recognition model may be derived from a neural network, a set of predetermined filters, or a comparison with a library of data stored in memory 120. The image recognition model may receive images from sensor 614 or other sensors of sensor units 114 and identify features or objects depicted within the image. The image recognition model may further output an action for the robot 102 to execute to disinfect identified objects. The image recognition model may be further configured to identify humans or animals such that the spray or UV light is not incident upon the humans or animals. The image recognition model may also be embodied on an external server communicatively coupled to the robot 102 via communications units 116, wherein the server receives images captured by the robot 102, processes the images to identify objects/features depicted therein, and communicates the identified features and corresponding cleaning action to the robot 102.

According to at least one non-limiting exemplary embodiment, robot 102 may be equipped with disinfectant means for use by humans. For example, sprayer 602 may be illustrative of a hand sanitizer or soap dispenser, wherein detection of the human may cause the robot 102 to dispense the hand sanitizer to the human. Dispensing of the hand sanitizer or soap may further require the human to provide an input to user interface units 116 (e.g., pressing of a button, use of a presence sensor beneath the hand sanitizing dispensing means, etc.). Alternatively, the controller 118 may recognize a gesture of a human, such as a human presenting an open palm to the robot, to determine a request to dispense hand sanitizer to the human.

According to at least one non-limiting exemplary embodiment, some objects may be disinfected using both UV light and a disinfectant spray, wherein the "actions" column may comprise both disinfecting actions.

FIG. 7 illustrates a computer-readable map 700, viewed from a top-down perspective, produced by a controller 118 of a robot 102 during navigation of a route 704, according to an exemplary embodiment. The robot 102 has been illustrated in three locations along the route 704. The computer-readable map 700 may include a plurality of pixels. Route 704 may begin at a marker 702 comprising a feature within the environment such as a quick-response code, a barcode, or other feature detectable by sensor units 114. The robot 102 may be configured to utilize e.g. two UV light sources 204 to emit UV light incident upon surfaces of nearby objects, the UV light emission pattern being shown by lines 306 as a concentrated column or point of high intensity UV light.

Each pixel of the map 700 may correspond to a discrete region in the environment of the robot 102. The pixels may be encoded with information corresponding to the environment of the robot 102, such as the presence of objects 706 or lack thereof. The pixels may be further encoded with a cleaning parameter value. The cleaning parameter value may range from zero to a maximum value N, wherein a pixel comprising a low cleaning parameter value may correspond to a region of the environment represented by the pixel being recently disinfected or cleaned and a high cleaning parameter value may correspond to the region having not been cleaned for a period of time. One skilled in the art may appreciate that a high cleaning parameter value may refer to either a recently disinfected or poorly disinfected region without limitation, wherein the high cleaning parameter value corresponding to a poorly disinfected region is not intended to be limiting.

Controller 118 of the robot 102 may receive data from navigation units 106 such that the robot 102 is localized on the computer-readable map 700 at all times during navigation of route 704. During the navigation, the controller 118 may utilize UV light sources 204 and/or sprayers 602 to disinfect surfaces of objects 706 and/or other objects/surfaces. As the robot 102 moves along route 704, humans 314 may pass nearby the robot 102 and cause a change in the emission pattern of the UV light from sources 204. Controller 118 may track these changes to the emission pattern during navigation and store the changes in memory 120 such that a total area disinfected may be calculated. The total disinfected area may correspond to a number of pixels on the map 700 that have been disinfected (e.g., pixels within the emission pattern of the UV light or have been sprayed with a disinfectant spray). In some embodiments, robot 102 may comprise a floor-cleaning robot, wherein the controller 118 may further track the area of the floor which has been cleaned. Pixels of the map 700 which have been disinfected by either UV light sources 204 and/or sprayer 602 may comprise a cleaning parameter value of approximately zero or other small number For example, areas not disinfected when a human is nearby may be identified or tracked based on a high cleaning parameter value associated with the pixels of map 700 which represent the areas.

It may be advantageous for the robot 102 to determine when route 704 should be executed based on a requirement for disinfection of the environment. FIG. 8 illustrates a graph 800 of a cleaning parameter value for a single pixel of the map 700, according to an exemplary embodiment. The horizontal axis of graph 800 is time and the vertical axis is the cleaning parameter value. The region of space represented by the pixel may be illuminated by the UV light or sprayed with a disinfectant at a time $t_D$ while the robot 102 navigates route 704. Upon the region corresponding to the pixel being disinfected, the cleaning parameter value of the pixel may be set to zero or a predetermined number (e.g., 0.1% of the maximum value, or larger). The cleaning parameter may grow as an exponential function corresponding to exponential growth of pathogens within the environment. The growth rate of the function may be predetermined or based on growth rates of known pathogens; however, it is appreciated that the growth rate may be intentionally overestimated to ensure adequate cleaning (i.e., configure a margin of safety).

Graph 800 may include a threshold 802 of a predetermined maximum value N. If the cleaning parameter of the pixel grows to reach the threshold N, the pixel may be marked as a "require cleaning" pixel on the map 700. The controller 118 of the robot 102 may subsequently execute the route 704 to disinfect the environment upon a threshold number of pixels comprising a cleaning parameter which reaches threshold 802. A pixel assigned by the controller as not disinfected because of the presence of a human during navigation of the route 704 may be arbitrarily assigned a high cleaning parameter, so that it may reach threshold 802 without reference to a growth rate of pathogens in the environment.

According to at least one non-limiting exemplary embodiment, the growth of the cleaning parameter may exceed threshold 802. The robot 102 may execute route 704 to disinfect the environment upon a summation of the cleaning parameters of all pixels of the map 700 reaching a threshold value.

According to at least one non-limiting exemplary embodiments, two or more robots 102 may operate within the same environment and disinfect, at least in part, the same objects 706. The robots 102 may utilize respective communications units 116 to communicate with each other during operation, the communications may be based in part on regions, represented by pixels on a computer-readable map, of the environment which have been disinfected and a time at which the regions were disinfected. The time may be utilized to calculate values for cleaning parameters for each pixel of the computer-readable maps used by the two or more respective robots 102.

According to at least one non-limiting exemplary embodiment, the controller 118 may produce a computer-readable map representing the environment, similar to map 700, wherein pixels of the map are encoded with a color value which represents the value of the cleaning parameter. The color values may range from a minimum value (e.g., white in greyscale representation, blue in RGB representation, etc.) to a maximum value (e.g., grey in greyscale representation, red in RGB representation, etc.), wherein the color values correspond to the value of the cleaning parameter associated with each pixel. For example, the map may be displayed onto a user interface unit 114 to a human operator such that the operator may readily visualize the areas within the environment which need disinfection, have been disinfected recently, or will need disinfection in the future. In some embodiments, the user interface unit 114 displaying the computer-readable map may further include a slider, button, or other graphical user interface element which enables the human operator to view the growth of "dirtiness" (i.e., growth of the cleaning parameter) over time represented by pixels of the displayed map changing color.

Figure 9:
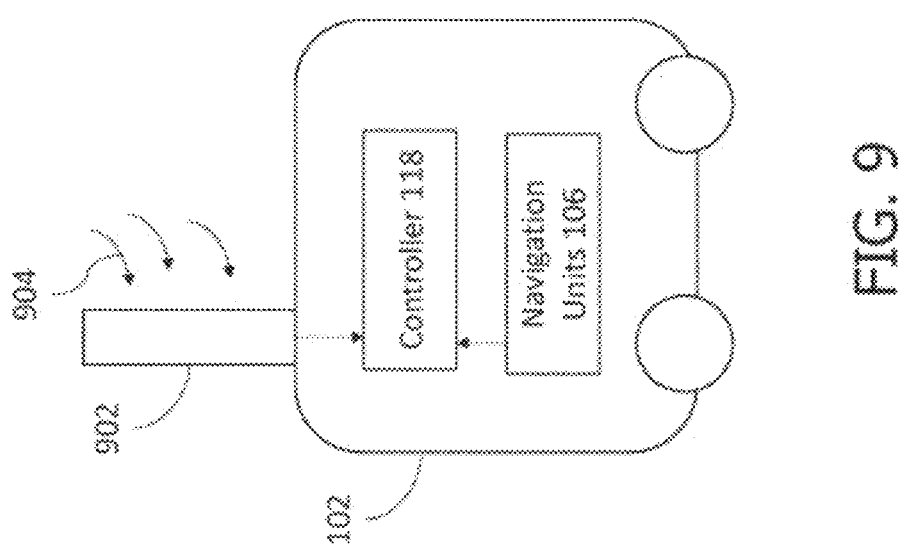
FIG. 9 illustrates a robot utilizing an air purifier to locate and map pathogens within its environment, according to an exemplary embodiment.

FIG. 9 illustrates a robot 102 comprising an air purifier 902, according to an exemplary embodiment. Robot 102 may operate within a hospital, elder care facility, or other environment wherein air sanitation is desired. Air purifier 902 may comprise one or more filters configured to filter incoming air, shown by arrows 904, of pathogens and bacteria. The controller 118 of the robot 102 may analyze the filters using one or more sensor units (e.g., a spectrometer) to identify pathogens within the filters of the air purifier 902. The controller 118 may additionally utilize data from navigation units 106 to localize itself within the environment. The controller 118 may correlate its position with any identified pathogens detected within the air purifier 902 and subsequently map the locations where the pathogens were filtered on a computer-readable map (e.g., 700). The mapped pathogens may be denoted using a specialized encoding of the pixels of the map or may set the cleaning parameter value of the pixels representing the locations to the threshold 802 value.

According to at least one non-limiting exemplary embodiment, the filters of the air purifier 902 may be analyzed subsequent navigation of a route. Accordingly, any detected pathogens may be correlated to locations of the robot 102 during navigation of the route.

According to at least one non-limiting exemplary embodiment, air purifier 902 may comprise a plurality of interchangeable filters which are replaced as the robot 102 navigates its environment. The controller 118 may automatically interchange used filters for new ones to ensure the filtered air is free of pathogens. Using data from navigation units 106, the controller 118 may determine locations where respective filters of the plurality were used. Accordingly, upon detection of pathogens within the used filters, the controller 118 may correlate the detected pathogens to locations where the used filter was utilized by the air purifier 902, and subsequently map the locations of the detected pathogens. The mapped locations may comprise a region on the computer-readable map.

Upon mapping of the pathogens based on detected pathogens within filters of the air purifier 902, the controller 118 may suggest to human operators one or more routes the robot 102 should execute to disinfect specific portions of the environment comprising the detected pathogens. Alternatively, the robot 102 may begin execution of the one or more routes upon detection of the pathogens without user input. The robot 102 may utilize UV lights 204 to disinfect the environment or a disinfectant spray, as discussed above.

It may be appreciated that the air purifier embodiment may be instantiated on a robot 102 separate from a robot configured with a UV emission module and/or a disinfectant spray module. For example, an air purifier robot may navigate a different route through an environment than that of a UV emission robot because it may not need to localize near surfaces that need disinfecting. In such embodiments, the pathogen map generated by the air purifier embodiment may be communicated to a disinfectant robot directly, via a network such as on a server, cloud or via notification to a human operator that can instruct a disinfectant robot to execute the one or more routes. In other embodiments the air purifier unit may be instantiated on a robot also configured with a UV emission module and/or a disinfectant spray module.

According to at least one non-limiting exemplary embodiment, a robot 102 may utilize data from sensor units 114 to detect humans in close proximity to each other to encourage social distancing by emitting a noise or visual display (e.g., blinking a light) upon detection of the humans within a threshold distance to each other. The robot 102 may further adapt its motions to avoid encouraging humans to move closer to each other by, for example, providing more space between shelves in an aisle for the humans to pass the robot 102 or avoiding crowded areas. In some instances, the robot 102 may block off entrances to avoid a threshold number of humans entering a room or building and subsequently move to allow more humans to enter upon detection of humans leaving the room or building. According to at least one non-limiting exemplary embodiment, robots 102 may be configurable to move objects from one location to another. These robots 102 may hold the objects within compartments or chambers, tug the objects behind the robots 102 (e.g., using a latch), carry objects using a loading deck, or other means of transporting items from one location to another. In some embodiments, the robots 102 may be equipped with UV lights 204 configurable to emit UV light incident upon the objects being carried, pulled, pushed, or otherwise transported by the robots 102. For example, a robot 102 may hold objects within an internal compartment, wherein the compartment may include a UV light 204 which disinfects the compartment and objects stored therein prior to the robot 102 transporting the object to a desired destination. As another example, a robot 102 may pull objects behind it, wherein the robot 102 may include rear facing UV light 204 incident upon the objects being pulled.

According to at least one non-limiting exemplary embodiment, the power supply 122 of robots 102 may be rechargeable without being detached from the robot 102 (i.e., without human assistance), wherein the robot 102 may navigate to a charging station to recharge power supply 122. The charging station may include one or more wired charging means (e.g., USB, wall-plug connectors, coaxial cables, etc.) or wireless charging means (e.g., inductive charging). The robot 102 may operate within crowded environments, such as grocery stores, hospitals, malls, farms (e.g., crowded with animals), markets, and the like, wherein the robot 102 itself may encounter pathogens. Accordingly, the charging station may be equipped with UV light sources 204 to disinfect the surfaces of robot 102 while power supply 122 recharges. In some embodiments, the charging station may include an enclosed room or space which houses the robot 102 therein during charging, wherein the entire room or space may be illuminated with UV light. In some embodiments, directional UV light sources 204 may be configured such that emitted UV light is only incident on the robot 102 body and not the surrounding environment. In some embodiments, the UV lights are disabled upon any of (i) the power supply 122 being fully recharged, (ii) the robot 102 resuming autonomous operation (e.g., upon a threshold number of pixels of a computer-readable map 700 comprising a cleaning parameter value equal to threshold 802), or (iii) a human being present nearby the charging station.

It will be recognized that while certain aspects of the disclosure are described in terms of a specific sequence of steps of a method, these descriptions are only illustrative of the broader methods of the disclosure, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the disclosure disclosed and claimed herein.

While the above detailed description has shown, described, and pointed out novel features of the disclosure as applied to various exemplary embodiments, it will be understood that various omissions, substitutions, and changes in the form and details of the device or process illustrated may be made by those skilled in the art without departing from the disclosure. The foregoing description is of the best mode presently contemplated of carrying out the disclosure. This description is in no way meant to be limiting, but rather should be taken as illustrative of the general principles of the disclosure. The scope of the disclosure should be determined with reference to the claims.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments and/or implementations may be understood and effected by those skilled in the art in practicing the claimed disclosure, from a study of the drawings, the disclosure and the appended claims.

It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open-ended as opposed to limiting. As examples of the foregoing, the term "including" should be read to mean "including, without limitation," "including but not limited to," or the like; the term "comprising" as used herein is synonymous with "including," "containing," or "characterized by," and is inclusive or open-ended and does not exclude additional, unrecited elements or method steps; the term "having" should be interpreted as "having at least;" the term "such as" should be interpreted as "such as, without limitation;" the term 'includes" should be interpreted as "includes but is not limited to;" the term "example" or the abbreviation "e.g." is used to provide exemplary instances of the item in discussion, not an exhaustive or limiting list thereof, and should be interpreted as "example, but without limitation;" the term "illustration" is used to provide illustrative instances of the item in discussion, not an exhaustive or limiting list thereof, and should be interpreted as "illustration, but without limitation;" adjectives such as "known," "normal," "standard," and terms of similar meaning should not be construed as limiting the item described to a given time period or to an item available as of a given time, but instead should be read to encompass known, normal, or standard technologies that may be available or known now or at any time in the future; and use of terms like "preferably," "preferred," "desired," or "desirable," and words of similar meaning should not be understood as implying that certain features are critical, essential, or even important to the structure or function of the present disclosure, but instead as merely intended to highlight alternative or additional features that may or may not be utilized in a particular embodiment. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise. The terms "about" or "approximate" and the like are synonymous and are used to indicate that the value modified by the term has an understood range associated with it, where the range may be ±20%, ±15%, ±10%, ±5%, or ±1%. The term "substantially" is used to indicate that a result (e.g., measurement value) is close to a targeted value, where close may mean, for example, the result is within 80% of the value, within 90% of the value, within 95% of the value, or within 99% of the value. Also, as used herein "defined" or "determined" may include "predefined" or "predetermined" and/or otherwise determined values, conditions, thresholds, measurements, and the like.

What is claimed is:

1. A robotic device, comprising:
   an ultraviolet emission source configured to emit UV light to kill at least one of germs, viruses, and bacteria, the ultraviolet emission source is an attachable module configured to be attached to the robotic device;
   and a memory comprising computer-readable instructions stored thereon; and
   at least one controller configured to execute the computer-readable instructions to,
   disinfect an environment using at least one of an ultraviolet (UV) light or a disinfectant spray;
   detect, by at least one sensor, a human being in a path traveled by the robotic device based on sequential images captured by the at least one sensor, the at least one sensor coupled to the robotic device,
   predict a path traveled by the human being by the at least one sensor coupled to the robotic device,
   avoid directing the ultraviolet light or the disinfectant spray towards the human being by adjusting the UV light or the disinfectant spray if the path traveled by the human being is in the path traveled by the robotic device, and
   change behavior of the robotic device upon detection of the attachment of the ultraviolet emission source,
   wherein the ultraviolet emission source comprises at least two UV lights, wherein each of the at least two UV lights are configured to emit UV light on either side of the robotic device, the at least two UV lights are configured to disinfect objects adjacent to the robotic device while avoiding the human being.

2. The device of claim 1, wherein the at least one controller is further configured to execute the computer-readable instructions to orient the robotic device such that field of view of the at least two UV lights encompasses objects or surfaces adjacent to the robotic device.

3. The device of claim 1, wherein the robotic device comprises a plurality of cylindrical UV lights configured to emit UV lights in a plurality of directions.

4. The device of claim 3, wherein the controller is further configured to execute the computer-readable instructions to,
   modulate the UV lights by amplifying or negating the UV lights,
   enable direction of the UV lights,
   change intensity of the UV lights, and
   selectively turn on and turn off the UV lights.

5. The device of claim 1, wherein the robotic device comprises an articulated arm configured to adjust position and orientation of an ultraviolet emission source.

6. The device of claim 1, wherein the robotic device comprises a plurality of extendable and retractable features configured to position UV light sources.

7. The device of claim 6, wherein the plurality of extendable and retractable features comprise actuated portions of the robotic device configured to extend laterally such that the UV light sources are utilized to disinfect a surface including at least one of floor, countertops, tables, and chairs.

8. The device of claim 1, wherein the controller is further configured to execute the computer-readable instructions to, navigate the robotic device on a route along a trajectory, and utilize the UV light to disinfect surfaces of objects positioned along the trajectory.

9. The device of claim 1, wherein the controller is further configured to execute the computer-readable instructions to,
identify the human being along a trajectory traveled by the robotic device based on gait pattern of the human being, and
adjust emission of UV light upon detection of the human being such that the UV light does not interfere with the human being along the trajectory.

10. The device of claim 1, wherein the controller is further configured to execute the computer-readable instructions to,
selectively activate one of at least two UV lights coupled to the robotic device, the selective activation of a respective one of the two UV light source is based on location of object with respect to the robotic device.

11. The device of claim 10, wherein the at least two UV lights are configured to emit light based on shape and size of the object.

12. A robot, comprising:
an ultraviolet emission source configured to emit UV light to kill at least one of germs, viruses, and bacteria, the ultraviolet emission source is an attachable module configured to be attached to the robot;
a non-transitory computer-readable storage medium comprising computer-readable instructions stored thereon; and
a controller configured to execute the computer-readable instructions to,
update a footprint of the robot upon detection of attachment of a
sprayer module, the sprayer module being configured to emit a mist of disinfectant solution into an environment, the footprint comprises an area corresponding to a digital representation of the area occupied by the robot, the update of the footprint includes comprises an increase in the area of the footprint;
detect, by at least one sensor. a human being in a path traveled by the robot based on sequential images captured by the at least one sensor, the at least one sensor coupled to the robot,
predict a path traveled by the human being by the at least one sensor coupled to the robot, and
deactivate the sprayer module if the path traveled by the human being is in the traveled path by the robot,
change behavior of the robotic device upon detection of attachment of the ultraviolet emission source,
wherein the ultraviolet emission source comprises at least two UV lights. wherein each of the at least two UV lights are configured to emit UV light on either side of the robot, the at least two UV lights are configured to disinfect objects adjacent to the robot while avoiding the human being.

13. The robot of claim 12, wherein the controller is further configured to execute the computer-readable instructions to,
learn a route via user demonstration by recording motions and actions of the robot while the robot operates under manual control, the motions and actions correspond to the learned behaviors and include at least one activation and deactivation of the sprayer module at one or more locations; and
autonomously recreate the route by replicating the motions and either activating or-deactivating the sprayer module at the one or more locations.

14. The robot of claim 12, wherein, the robot is configured to perform at least one of sweeping floors, vacuuming floors, scrubbing floors, or transporting items from one location to another while the controller is activating or deactivating the sprayer module.

* * * * *